(12) United States Patent
Gaffney et al.

(10) Patent No.: US 11,306,301 B2
(45) Date of Patent: Apr. 19, 2022

(54) POLYPEPTIDE HAVING XYLANASE ACTIVITY

(71) Applicants: UNIVERSITY OF LIMERICK, Limerick (IE); MONAGHAN MUSHROOMS IRELAND UNLIMITED COMPANY, County Monaghan (IE)

(72) Inventors: Darragh Gaffney, Cavan (IE); Kelly Dwyer, Tipperary (IE); Gary Walsh, Limerick (IE); Alison Winger, County Cork (IE)

(73) Assignees: MONAGHAN MUSHROOMS IRELAND UNLIMITED COMPANY, County Monaghan (IE); UNIVERSITY OF LIMERICK, Limerick (IE)

( * ) Notice: Subject to any disclaimer, the term of this patent is extended or adjusted under 35 U.S.C. 154(b) by 0 days.

(21) Appl. No.: 16/971,836

(22) PCT Filed: Feb. 25, 2019

(86) PCT No.: PCT/EP2019/054636
§ 371 (c)(1),
(2) Date: Aug. 21, 2020

(87) PCT Pub. No.: WO2019/162516
PCT Pub. Date: Aug. 29, 2019

(65) Prior Publication Data
US 2021/0079369 A1    Mar. 18, 2021

(30) Foreign Application Priority Data
Feb. 23, 2018 (EP) .................................. 18158430

(51) Int. Cl.
*C12N 9/24* (2006.01)
*C12N 15/52* (2006.01)
(Continued)

(52) U.S. Cl.
CPC ............. *C12N 9/2482* (2013.01); *C12N 1/14* (2013.01); *C12N 1/16* (2013.01); *C12N 1/20* (2013.01);
(Continued)

(58) Field of Classification Search
None
See application file for complete search history.

(56) References Cited

U.S. PATENT DOCUMENTS

| 2016/0083761 A1* | 3/2016 | McBrayer | ...... C12Y 302/01008 |
| | | | 435/99 |
| 2021/0079369 A1* | 3/2021 | Gaffney | ............... C12N 9/2482 |

FOREIGN PATENT DOCUMENTS

| WO | WO2007091231 A1 | 8/2007 |
| WO | WO2007091231 A9 | 8/2007 |

(Continued)

OTHER PUBLICATIONS

Tuohy M G et al., "Characterization of the Individual Components of the Xylanolytic Enzyme System of Talaromyces Emersonii", Bioresource Technology, Elsevier, Janury 1, 1994, pp. 37-42, vol. 50, No. 1.
(Continued)

*Primary Examiner* — Richard C Ekstrom
(74) *Attorney, Agent, or Firm* — Greer, Burns & Crain, Ltd.

(57) ABSTRACT

The present invention relates to an isolated polypeptide having xylanase activity. Also disclosed are isolated polynucleotides encoding the polypeptide, recombinant host cells expressing the polypeptide, and methods for degrading lignocellulosic biomass using the polypeptide. He invention finds utility in the production of biofuels, in the paper and
(Continued)

pulp industry, in clothing or leather softening, in the food industry such as baking, etc.

21 Claims, 5 Drawing Sheets

Specification includes a Sequence Listing.

(51) Int. Cl.
  *C12N 1/14* (2006.01)
  *C12N 1/16* (2006.01)
  *C12N 1/20* (2006.01)
  *C12P 7/10* (2006.01)
(52) U.S. Cl.
  CPC ............... *C12N 15/52* (2013.01); *C12P 7/10* (2013.01); *C12Y 302/01008* (2013.01)

(56) References Cited

FOREIGN PATENT DOCUMENTS

| WO | WO2014138983 A1 | 9/2014 |
| WO | WO2014202616 A2 | 12/2014 |
| WO | WO2014202616 A3 | 12/2014 |

OTHER PUBLICATIONS

Tuohy M G et al., The Xylan-Degrading Enzyme System of Talaromyces Emersonii: Novel Enzymes with Activity Against Aryl Beta-D-Xylosidesand Unsubstituted Xylans, Biochemical Journal, Mar. 1, 1993, pp. 515-523, vol. 290, No. 2.

Database UniProt [on-line], "RecName: Full=Beta-xylanase", Jun. 24, 2015, pp. 1-2.

* cited by examiner

SEQUENCE LISTING

```
<160> NUMBER OF SEQ ID NOS: 7

<210> SEQ ID NO 1
<211> LENGTH: 362
<212> TYPE: PRT
<213> ORGANISM: Rasamsonia emersonii

<400> SEQUENCE: 1

Met Arg Leu Ser Pro Ser Leu Ile Phe Val Pro Leu Val Thr Pro Ala
1               5                   10                  15

Phe Thr Leu Leu Phe Asn Ser Asn Leu Thr Ser Pro Pro Trp Leu Asn
            20                  25                  30

Asp Leu Ala Gln Arg Arg Gly Lys Leu Trp Phe Gly Thr Ala Ala Asp
        35                  40                  45

Ile Pro Gly Pro Glu Gln Gln Asp Thr Asn Tyr Met Thr Ile Leu Asn
    50                  55                  60

Asp Thr Lys Ile Phe Gly Glu Leu Thr Pro Ala Asn Tyr Met Lys Phe
65                  70                  75                  80

Glu Tyr Thr Glu Pro Ser Pro Asn Val Phe Asn Tyr Ser Gly Gly Asp
                85                  90                  95

Thr Ile Leu Ala Ile Ala Glu Asn His Gly Lys Arg Val Arg Cys His
            100                 105                 110

Asn Leu Ile Trp Val Ser Gln Leu Pro Asp Trp Val Val Asn Gly Ser
        115                 120                 125

Trp Thr Ala Ala Ser Leu Thr Ala Val Met Lys Thr His Ile Thr Asn
    130                 135                 140

Leu Ile Thr His Trp Gly Gly Arg Cys Tyr Ser Trp Asp Val Val Asn
145                 150                 155                 160

Glu Ala Leu Ala Ala Asn Gly Ser Trp Ala Ser Ser Ile Trp Tyr Asp
                165                 170                 175

Thr Ile Gly Pro Glu Tyr Phe Phe Leu Ala Tyr Arg Phe Ala Gln Glu
            180                 185                 190
```

Ala Val Glu Lys Thr Gly Gln Asp Ile Lys Leu Tyr Tyr Asn Asp Tyr
    195                 200                 205

Gly Ile Glu Ala Pro Gly Pro Lys Thr Thr Ala Ala Tyr Asn Leu Val
    210                 215                 220

Lys Glu Leu Gln Ala Arg Gly Ile Arg Ile Asp Gly Val Gly Leu Glu
225                 230                 235                 240

Ser His Phe Glu Val Gly Ala Thr Pro Ser Lys Asp Ala Gln Val Glu
                245                 250                 255

Ala Lys Gln Gly Phe Leu Asp Leu Gly Val Asp Val Val Thr Glu
            260                 265                 270

Leu Asp Val Arg Phe Pro Glu Gly Pro Phe Tyr Thr Ala Ala Gly Glu
    275                 280                 285

Lys Gln Gln Ala Gln Asp Tyr Tyr Asp Thr Val Ala Ser Cys Val Glu
    290                 295                 300

Val Gly Pro Arg Cys Val Gly Ile Thr Val Trp Asp Phe Asp Asp Ala
305                 310                 315                 320

Tyr Ser Trp Val Pro Ser Ser Phe Pro Gly Gln Gly Ala Ala Asp Leu
                325                 330                 335

Tyr Asn Gly Thr Leu Gln Arg Lys Pro Ala Tyr Ala Val Ala Glu
            340                 345                 350

Ala Leu Gln Gly Val Ser Cys Ser Val Cys
            355                 360

<210> SEQ ID NO 2
<211> LENGTH: 1089
<212> TYPE: DNA
<213> ORGANISM: Rasamsonia emersonii

<400> SEQUENCE: 2
atgcgtctct ctccgtcttt aatattcgta ccgctggtca caccagcctt tacattgcta      60
ttcaactcga acctcacatc tcctccatgg ctcaatgatc tcgcacagag gcgtggcaag     120
ctgtggtttg gcacggcagc tgacatcccc ggtccagagc agcaggatac gaactacatg     180
accatcctga tgatacgaa gatatttggg gaattgacgc ctgcgaatta tatgaagttc     240
gaatacactg aaccatcgcc caatgtcttc aactactctg gcggcgacac catcctggcc     300
atcgccgaaa accacggcaa gcgcgttcgc tgccacaacc tcatctgggt cagccagctg     360
cccgactggg tggtgaacgg cagctggaca gcggcgagcc tcacagcggt gatgaagacg     420
cacatcacga acctgatcac gcactgggga gggcggtgct actcgtggga cgtggtcaac     480
gaggcgctgg cggcgaacgg gtcgtgggcg tccagcatct ggtacgacac catcgggccc     540
gagtacttct cctcgcgta ccggtttgcg caggaggcgg tcgaaaagac cggccaggac     600
atcaagctgt actacaatga ctcgggatc gaggcgcccg gtcccaagac gacggcggcg     660
tacaacctgg tcaaggagct gcaggcgcga ggcatccgga tcgatggcgt ggggttggag     720
tcgcatttcg aagtgggcgc gacgccatcc aaggacgcgc aggttgaggc caagcagggg     780 ttttttggatc tggggtcga tgttgtcgtc acggagctgg atgtcagatt cccggagggg     840
ccgttctaca cggcggcggg tgagaagcag caggcgcagg actattatga tacggtggcg     900
agctgcgtgg aggttggtcc tcggtgtgtg ggcatcacgg tgtgggattt tgacgatgcg     960
tattcgtggg tgccgtcatc gtttcctgga cagggagcgg ctgatctgta taatgggacg    1020
ttgcagcgga agccggcgta ctatgcggtg gcagaggcat tgcaggggt gagttgtagt    1080 gtgtgctaa                                                            1089

<210> SEQ ID NO 3
<211> LENGTH: 1089
<212> TYPE: DNA
<213> ORGANISM: Rasamsonia emersonii

<400> SEQUENCE: 3

```
atgaggctgt caccatccct aatattcgta cctcttgtga cacccgcttt caccttactg      60
ttcaattcca acctaacgtc cccccttgg cttaatgatc tggcacagag gaggggtaag     120
ttatggtttg gtaccgccgc agatattccc ggtcctgagc aacaagacac aaactatatg    180
acgatactta atgatacaaa gattttcgga gaactaactc cagccaacta catgaaattt    240
gagtacacgg agcccagtcc caatgtcttc aattacagtg gcggtgatac tattctggca    300
attgcagaaa tcatggtaa aagggttagg tgtcataatc ttatttgggt tcacaacttc    360
cccgattggg ttgtgaacgg ttcttggact gccgcttccc taactgctgt aatgaagaca    420
catattacga atttaatcac acattgggga ggtcgttgtt acagttggga tgtcgttaac    480
gaagctctgg cagccaacgg ttcatgggct agttcaatct ggtacgacac cataggacca    540
gagtatttct tcctagcata cagattcgct caggaggctg ttgagaaaac cggccaagat    600
atcaaattgt actataacga ctatggcatt gaagctcctg gtcccaagac aactgcagcc    660
tataatctgg tcaaggaact tcaagcaaga ggaatccgta tcgacggcgt cggtttggag    720
tctcattttg aggtgggagc aaccccttcc aaggatgctc aggttgaagc taaacaaggt    780
tttcttgacc tgggagtaga cgttgtcgtt acggagttgg atgtccgttt ccccgagggc    840
cctttttaca ccgcagctgg agagaagcaa caggcccaag actattacga cacagttgca    900
agttgcgtag aagtcggccc caggtgcgtg gcattactg tctgggactt cgacgacgct    960
tactcttggg tcccttcctc ctttcccggc caaggtgccg cagacctata caatggtact   1020
ttacagagga agcctgctta ctatgctgtg gcagaggcac tacaaggcgt gtcatgcagt   1080
gtctgctaa                                                            1089
```

<210> SEQ ID NO 4
<211> LENGTH: 941
<212> TYPE: DNA
<213> ORGANISM: Pichia pastoris

<400> SEQUENCE: 4

```
agatctaaca tccaaagacg aaaggttgaa tgaaacctt ttgccatccg acatccacag      60
gtccattctc acacataagt gccaaacgca acaggagggg atacactagc agcagaccgt    120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggccccctg gcgaggttca tgtttgttta     300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcggca taccgtttgt    540
cttgtttggt attgattgac gaatgctcaa aaataatctc attaatgctt agcgcagtct    600
ctctatcgct tctgaacccc ggtgcacctg tgccgaaacg caaatgggga acacccgct     660
ttttggatga ttatgcattg tctccacatt gtatgcttcc aagattctgg tgggaatact    720
```

```
gctgatagcc taacgttcat gatcaaaatt taactgttct aaccctact tgacagcaat      780 atataaacag aaggaagctg ccctgtctta aacctttttt tttatcatca ttattagctt     840
actttcataa ttgcgactgg ttccaattga caagcttttg attttaacga cttttaacga     900
caacttgaga agatcaaaaa acaactaatt attcgaaacg a                         941
```

```
<210> SEQ ID NO 5
<211> LENGTH: 192
<212> TYPE: DNA
<213> ORGANISM: Rasamsonia emersonii

<400> SEQUENCE: 5
agcaccacct acatcatctc gccgacgacg tctgtcggaa cgggcacgac gacctcgagc      60
ggcggaagcg gcggcacgac tggcgtggcc cagcattggg agcagtgcgg tggactgggc    120
tggactggtc cgacggtttg cgcaagtggc tacacttgca ctgtcatcaa tgagtattac    180
tcgcagtgtc tg                                                        192
```

```
<210> SEQ ID NO 6
<211> LENGTH: 29
<212> TYPE: DNA
<213> ORGANISM: Unknown
<220> FEATURE:
<223> OTHER INFORMATION: Synthetic primer sequence

<400> SEQUENCE: 6
gggggaattc ttgctattca actcgaacc                                       29
```

```
<210> SEQ ID NO 7
<211> LENGTH: 31
<212> TYPE: DNA
<213> ORGANISM: Unknown
<220> FEATURE:
<223> OTHER INFORMATION: Synthetic primer sequence

<400> SEQUENCE: 7
ggggtctaga gtgcacacac tacaactcac c                                    31
```

POLYPEPTIDE HAVING XYLANASE ACTIVITY

CROSS-REFERENCE TO RELATED APPLICATIONS

This application is the U.S. National phase application corresponding to PCT/EP2019/054636 which was assigned an international filing date of Feb. 25, 2019 and associated with publication WO 2019/162516 A1 and which claims priority to EP 18158430.1, filed Feb. 23, 2018, the disclosures of which are expressly incorporated herein by reference.

FIELD OF THE INVENTION

The present invention relates to an isolated polypeptide having xylanase activity. Also disclosed are isolated polynucleotides encoding the polypeptide, recombinant host cells expressing the polypeptide, and methods for degrading lignocellulosic biomass using the polypeptide.

BACKGROUND TO THE INVENTION

Lignocellulose biomass is the most abundantly available raw material on Earth for the production of biofuels, such as cellulosic bioethanol, which is a renewable transport fuel that can be produced, for example, from agricultural waste. The widespread deployment of biofuels is highly desirable to reduce greenhouse gas emissions, improve energy security, support economic growth and job creation, and is in line with global and European renewable energy strategy and policies.

The production of biofuels from lignocellulose biomass is however technically challenging. The process involves a number of steps including enzymatic hydrolysis of the cellulose and hemicellulose components of the lignocellulose biomass in order to release sugars for subsequent fermentation. Organisms that produce enzyme systems capable of degrading lignocellulose biomass are widely distributed in nature and include higher plants, fungi, and bacteria.

The enzymes typically used in production of biofuels from lignocellulose biomass include cellulases and hemicellulases, with pH and temperature optima usually at or near the hydrolysis conditions. Hydrolysis is usually undertaken at pH of 4.5-5.5 and a temperature of 45-55° C. However, conducting hydrolysis at temperatures above 55° C. could increase product solubility, facilitate higher substrate loadings, and reduce process liquid viscosity—which could contribute to the feasibility of the production of biofuels from lignocellulose biomass on an industrial scale.

In the baking industry, xylanase enzymes are used to alter the properties of dough. Wheat flour contains up to 4% arabinoxylans (a highly-branched hemicellulose found in both the primary and secondary cell walls of plants such as wheat, barley, oat, and rye—and comprising copolymers of arabinose and xylose). Some arabinoxylans are soluble, while the majority are coupled to wheat proteins (in an insoluble fraction), which is believed to reduce the elasticity of the gluten (and hence the dough). Xylanases added to the flour can improve the handling and stability of the dough by acting on the insoluble arabinoxylan fraction. Moreover, xylanase enzymes find similar utility in the paper and pulp industry, and animal feed sector.

A major disadvantage of current commercial enzymatic hydrolysis is reduced enzyme performance due to heat inactivation. As xylan is the single most abundant hemicellulose fraction in lignocellulose biomass, and the inclusion of xylanase enzyme is important in most hydrolysis reactions, the isolation and development of new thermo-active and thermostable xylanase enzymes is important for the development of feasible industrial hydrolysis reactions.

SUMMARY OF THE INVENTION

According to a first aspect of the present invention, there is provided an isolated polypeptide comprising the amino acid sequence:
MRLSPSLIFVPLVTPAFTLLFNSNLTSPPWLND-
LAQRRGKLWFGTAADIPGPEQQDTNYMTI
LNDTKIFGELTPANYMKFEYTEPSPNVF-
NYSGGDTILAIAENHGKRVRCHN-
LIWVSQLPDWV VNGSWTAASLTAVMKTHITN-
LITHWGGRCYSWDVVNEALAANGSWAS
SIWYDTIGPEYFFL AYRFAQEAVEKTGQDIK-
LYYNDYGIEAPGPKTTAAYNLVKELQAR-
GIRIDGVGLESHFEVGA TPSKDAQVEAKQGFLD-
LGVDVVVTELDVRFPEGPFYTAAGEKQQAQ
DYYDTVASCVEVGP RCVGITVWDFDDAY-
SWVPSSFPGQGAADLYNGTLQRKPAYYA-
VAEALQGVSCSVC,
or a fragment or analogue thereof.

Optionally, the isolated polypeptide comprises the amino acid sequence defined in SEQ ID NO:1, or a fragment or analogue thereof.

Optionally, the isolated polypeptide is encoded by a polynucleotide comprising the nucleic acid sequence:
ATGCGTCTCTCTCCGTCTTTAATAT-
TCGTACCGCTGGTCACACCAGCCTTTACAT-
TGCTA TTCAACTCGAACCTCACATCTCCTC-
CATGGCTCAATGATCTCGCACAGAGGC
GTGGCAA GCTGTGGTTTGGCACGGCAGCTGA-
CATCCCCGGTCCAGAGCAGCAGGA-
TACGAACTA CATGACCATCCTGAATGA-
TACGAAGATATTTGGGGAATTGACGCCT
GCGAATTATATGA AGTTCGAATACACTGAAC-
CATCGCCCAATGTCTTCAAC-
TACTCTGGCGGCGACACCATC CTGGC-
CATCGCCGAAAACCACGGCAAGCGCG
TTCGCTGCCACAACCTCATCTGGGTCA
GCCAGCTGCCCGACTGGGTGGT-
GAACGGCAGCTGGACAGCGGCGAGCCT-
CACAGCG GTGATGAAGACGCACAT-
CACGAACCTGATCACGCACTGGGGAGG
GCGGTGCTACTCG TGGGACGTGGT-
CAACGAGGCGCTGGCGGCGAACGGGTC
GTGGGCGTCCAGCATCTG GTACGACAC-
CATCGGGCCCGAGTACTTCTTCCTCGC
GTACCGGTTTGCGCAGGAGGC GGTCGAAAA-
GACCGGCCAGGACATCAAGCTGTACTA-
CAATGACTACGGGATCGAGGCG CCCGGTCC-
CAAGACGACGGCGGCGTACAACCT
GGTCAAGGAGCTGCAGGCGCGAGG CATCCG-
GATCGATGGCGTGGGGTTGGAGTCGCAT-
TTCGAAGTGGGCGCGACGCCATC
CAAGGACGCGCAGGTTGAGGC-
CAAGCAGGGGTTTTTGGATCTGGGGGTC-
GATGTTGT CGTCACGGAGCTGGATGTCAGAT-
TCCCGGAGGGGCCGTTCTACACGGCGGCGGGT-
GA
GAAGCAGCAGGCGCAGGACTATTATGA-
TACGGTGGCGAGCTGCGTGGAGGTTGGTCC
TCGGTGTGTGGGCATCACGGTGTGGGAT- TTTGACGATGCGTATTCGTGGGTGCCGTCA
TCGTTTCCTGGACAGGGAGCGGCT-
GATCTGTATAATGGGACGTTGCAGCG-
GAAGCCG GCGTACTATGCGGTGGCAGAGG-
CATTGCAGGGGGTGAGTTGTAGTGTGTGCTAA, or a fragment or variant thereof.

Optionally, the isolated polypeptide is encoded by a polynucleotide comprising the nucleic acid sequence defined in SEQ ID NO:2, or a fragment or variant thereof.

Optionally, the isolated polypeptide is encoded by a polynucleotide comprising the nucleic acid sequence:

ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAG GCC CAA GAC TAT TAC GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA, or a fragment or variant thereof.

Optionally, the isolated polypeptide is encoded by a polynucleotide comprising the nucleic acid sequence defined in SEQ ID NO:3, or a fragment or variant thereof.

According to a second aspect of the present invention, there is provided an isolated polynucleotide comprising the nucleic acid sequence:

ATGCGTCTCTCTCCGTCTTTAATAT-
TCGTACCGCTGGTCACACCAGCCTTTACAT-
TGCTA TTCAACTCGAACCTCACATCTCCTC-
CATGGCTCAATGATCTCGCACAGAGGCGT
GGCAA GCTGTGGTTTGGCACGGCAGCTGA-
CATCCCCGGTCCAGAGCAGCAGGA-
TACGAACTA CATGACCATCCTGAATGA-
TACGAAGATATTTGGGGAATTGACGCCT
GCGAATTATATGA AGTTCGAATACACTGAAC-
CATCGCCCAATGTCTTCAAC-
TACTCTGGCGGCGACACCATC CTGGC-
CATCGCCGAAAACCACGGCAAGCGCGT
TCGCTGCCACAACCTCATCTGGGTCA
GCCAGCTGCCCGACTGGGTGGT-
GAACGGCAGCTGGACAGCGGCGAGCCT-
CACAGCG GTGATGAAGACGCACAT-
CACGAACCTGATCACGCACTGGGGAG
GGCGGTGCTACTCG TGGGACGTGGT-
CAACGAGGCGCTGGCGGCGAACGGG
TCGTGGGCGTCCAGCATCTG GTACGACAC-
CATCGGGCCCGAGTACTTCTTCCTCG
CGTACCGGTTTGCGCAGGAGGC GGTCGAAAA-
GACCGGCCAGGACATCAAGCTGTACTA-
CAATGACTACGGGATCGAGGCG CCCGGTCC-
CAAGACGACGGCGGCGTACAACCT
GGTCAAGGAGCTGCAGGCGCGAGG CATCCG-
GATCGATGGCGTGGGGTTGGAGTCGCAT-
TTCGAAGTGGGCGCGACGCCATC
CAAGGACGCGCAGGTTGAGGC-
CAAGCAGGGGTTTTTGGATCTGGGGGTC-
GATGTTGT CGTCACGGAGCTGGATGTCAGAT-
TCCCGGAGGGGCCGTTCTACACGGCGGCGGGT-
GA
GAAGCAGCAGGCGCAGGACTATTATGA-
TACGGTGGCGAGCTGCGTGGAGGTTGGTCC
TCGGTGTGTGGGCATCACGGTGTGGGAT-
TTTGACGATGCGTATTCGTGGGTGCCGTCA
TCGTTTCCTGGACAGGGAGCGGCT-
GATCTGTATAATGGGACGTTGCAGCG-
GAAGCCG GCGTACTATGCGGTGGCAGAGG-
CATTGCAGGGGGTGAGTTGTAGTGTGTGCTAA, or a fragment or variant thereof.

Optionally, the isolated polynucleotide comprises the nucleic acid sequence defined in SEQ ID NO:2, or a fragment or variant thereof.

Optionally, the isolated polynucleotide comprises the nucleic acid sequence:

ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAG GCC CAA GAC TAT TAC

GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA, or a fragment or variant thereof.

Optionally, the isolated polynucleotide comprises the nucleic acid sequence defined in SEQ ID NO:3, or a fragment or variant thereof.

According to a third aspect of the present invention, there is provided a vector comprising the nucleic acid sequence:
ATGCGTCTCTCTCCGTCTTTAATAT-TCGTACCGCTGGTCACACCAGCCTTTACAT-TGCTA TTCAACTCGAACCTCACATCTCCTC-CATGGCTCAATGATCTCGCACAGAGGCG TGGCAA GCTGTGGTTTGGCACGGCAGCTGA-CATCCCCGGTCCAGAGCAGCAGGA-TACGAACTA CATGACCATCCTGAATGA-TACGAAGATATTTGGGGAATTGACGCCTG CGAATTATATGA AGTTCGAATACACTGAAC-CATCGCCCAATGTCTTCAAC-TACTCTGGCGGCGACACCATC CTGGC-CATCGCCGAAAACCACGGCAAGCGCGT TCGCTGCCACAACCTCATCTGGGTCA GCCAGCTGCCCGACTGGGTGGT-GAACGGCAGCTGGACAGCGGCGAGCCT-CACAGCG GTGATGAAGACGCACAT-CACGAACCTGATCACGCACTGGGGA GGGCGGTGCTACTCG TGGGACGTGGT-CAACGAGGCGCTGGCGGCGAACGG GTCGTGGGCGTCCAGCATCTG GTACGACAC-CATCGGGCCCGAGTACTTCTTCCTCGCG TACCGGTTTGCGCAGGAGGC GGTCGAAAA-GACCGGCCAGGACATCAAGCTGTACTA-CAATGACTACGGGATCGAGGCG CCCGGTCC-CAAGACGACGGCGGCGTACAACCTGG TCAAGGAGCTGCAGGCGCGAGG CATCCG-GATCGATGGCGTGGGGTTGGAGTCGCAT-TTCGAAGTGGGCGCGACGCCATC CAAGGACGCGCAGGTTGAGGC-CAAGCAGGGGTTTTTGGATCTGGGGGTC-GATGTTGT CGTCACGGAGCTGGATGTCAGAT-TCCCGGAGGGGCCGTTCTACACGGCG GCGGGTGA GAAGCAGCAGGCGCAGGACTAT-TATGATACGGTGGCGAGCTGCGTG-GAGGTTGGTCC TCGGTGTGTGGGCAT-CACGGTGTGGGATTTTGACGATGCG TATTCGTGGGTGCCGTCA TCGTTTCCTGGACAGGGAGCGGCT-GATCTGTATAATGGGACGTTGCAGCG-GAAGCCG GCGTACTATGCGGTGGCAGAGG-CATTGCAGGGGGTGAGTTGTAGTGTGTGCTAA, or a fragment or variant thereof.

Optionally, the vector comprises the nucleic acid sequence defined in SEQ ID NO:2, or a fragment or variant thereof.

Optionally, the vector comprises the nucleic acid sequence:
ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAA CAG GCC CAA GAC TAT TAC GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA, or a fragment or variant thereof.

Optionally, the vector comprises the nucleic acid sequence defined in SEQ ID NO:3, or a fragment or variant thereof.

Optionally, the vector further comprises the nucleic acid sequence:
AGCACCACCTACAT-CATCTCGCCGACGACGTCTGTCG-GAACGGGCACGACGACCTCGA GCGGCG-GAAGCGGCGGCACGACTGGCGTGGCCC AGCATTGGGAGCAGTGCGGTGGA CTGGGCTGGACTGGTCCGACGGTTTGC GCAAGTGGCTACACTTGCACTGTCATCAATG AGTATTACTCGCAGTGTCTG, or a fragment or variant thereof.

Optionally, the vector comprises the nucleic acid sequence defined in SEQ ID NO:5, or a fragment or variant thereof.

Optionally, the vector further comprises a promoter operatively linked to the nucleic acid sequence:
ATGCGTCTCTCTCCGTCTTTAATAT-TCGTACCGCTGGTCACACCAGCCTTTACATTGCTAT-TCAA CTCGAACCTCACATCTCCTCCATGGCTCAAT-GATCTCGCACAGAGGCGTGGCAAGCTGTGGTTT GGCACGGCAGCTGA-CATCCCCGGTCCAGAGCAGCAGGATACGAACTA-CATGACCATCCTGAAT GATACGAAGATATTTGGG-GAATTGACGCCTGCGAATTATATGAAGT TCGAATACACTGAACCAT CGCCCAATGTCTTCAAC-TACTCTGGCGGCGACACCATCCTGGC-CATCGCCGAAAACCACGGCA AGCGCGTTCGCTGC-CACAACCTCATCTGGGTCAGCCAGCTGCCCG ACTGGGTGGTGAACGGC AGCTGGACAGCGGCGAGCCTCACAGCGGTGAT-GAAGACGCACATCACGAACCTGATCACGCA CTGGGGAGGGCGGTGCTACTCGTGGGACGTGGT-CAACGAGGCGCTGGCGGCGAACGGGTCG TGGGCGTCCAGCATCTGGTACGACACCATCGGGCCCGAGTACTTCTTCCTCGCGTACCGGTTT GCGCAGGAGGCGGTCGAAAAGACCGGCCAGGACATCAAGCTGTACTACAATGACTACGGGAT CGAGGCGCCCGGTCCCAAGACGACGGCGGCGTACAACCTGGTCAAGGAGCTGCAGGCGCGA GGCATCCGGATCGATGGCGTGGGGTTGGAGTCGCATTTCGAAGTGGGCGCGACGCCATCCAAGGACGCGCAGGTTGAGGCCAAGCAGGGGTTTTTGGATCTGGGGGTCGATGTTGTCGTCACGG AGCTGGATGTCAGATTCCCGGAGGGGCCGTTCTACACGGCGGCGGGTGAGAAGCAGCAGGCGCAGGACTATTATGATACGGTGGCGAGCTGCGTGGAGGTTGGTCCTCGGTGTGTGGGCATCACG GTGTGGGATTTTGACGATGCGTATTCGTGGGTGCCGTCATCGTTTCCTGGACAGGGAGCGGCT GATCTGTATAATGGGACGTTGCAGCGGAAGCCGGCGTACTATGCGGTGGCAGAGGCATTGCAG GGGGTGAGTTGTAGTGTGTGCTAA; or the nucleic acid sequence defined in SEQ ID NO:2; or the nucleic acid sequence defined in SEQ ID NO:3; or the fragment or variant each thereof.

Optionally, the promoter comprises the nucleic acid sequence:
AGATCTAACATCCAAAGACGAAAGGTTGAATGAAACCTTTTTGCCATCCGACATCCACA GGTCCATTCTCACACATAAGTGCCAAACGCAACAGGAGGGGATACACTAGCAGCAGACCGTTGCAAACGCAGGACCTCCACTCCTCTTCTCCTCAACACCCACTTTTGCCATCGAAA AACCAGCCCAGTTATTGGGCTTGATTGGAGCTCGCTCATTCCAATTCCTTCTATTAGGC TACTAACACCATGACTTTATTAGCCTGTCTATCCTGGCCCCCTGGCGAGGTTCATGTT TGTTTATTTCCGAATGCAACAAGCTCCGCATTACACCCGAACATCACTCCAGATGAGGG CTTTCTGAGTGTGGGGTCAAATAGTTTCATGTTCCCCAAATGGCCCAAAACTGACAGTT TAAACGCTGTCTTGGAACCTAATATGACAAAAGCGTGATCTCATCCAAGATGAACTAAG TTTGGTTCGTTGAAATGCTAACGGCCAGTTGGTCAAAAAGAAACTTCCAAAAGTCGGCA TACCGTTTGTCTTGTTTGGTATTGATTGACGAATGCTCAAAAATAATCTCATTAATGCTTA GCGCAGTCTCTCTATCGCTTCTGAACCCCGGTGCACCTGTGCCGAAACGCAAATGGGG AAACACCCGCTTTTTGGATGATTATGCATTGTCTCCACATTGTATGCTTCCAAGATTCTG GTGGGAATACTGCTGATAGCCTAACGTTCATGATCAAAATTTAACTGTTCTAACCCCTACTTGACAGCAATATATAAACAGAAGGAAG CTGCCCTGTCTTAAACCTTTTTTTTATCATCATTATTAGCTTACTTTCATAATTGCGACTGGTTCCAATTGACAAGCTTTTGATTTTAACGA CTTTTAACGACAACTTGAGAAGATCAAAAAACAACTAATTATTCGAAACGA,
or a fragment or variant thereof.

Optionally, the promoter comprises the nucleic acid sequence defined in SEQ ID NO:4, or a fragment or variant thereof.

According to a fourth aspect of the present invention, there is provided a host cell comprising a vector comprising the nucleic acid sequence:

ATGCGTCTCTCTCCGTCTTTAATATTCGTACCGCTGGTCACACCAGCCTTTACATTGCTA TTCAACTCGAACCTCACATCTCCTCCATGGCTCAATGATCTCGCACAGAGGCGT GGCAA GCTGTGGTTTGGCACGGCAGCTGACATCCCCGGTCCAGAGCAGCAGGATACGAACTA CATGACCATCCTGAATGATACGAAGATATTTGGGGAATTGACGCCTG CGAATTATATGA AGTTCGAATACACTGAACCATCGCCCAATGTCTTCAACTACTCTGGCGGCGACACCATC CTGGCCATCGCCGAAAACCACGGCAAGCGCGTTCGCTGCCACAACCTCATCTGGGTCAGCCAGCTGCCCGACTGGGTGGTGAACGGCAGCTGGACAGCGGCGAGCCTCACAGCG GTGATGAAGACGCACATCACGAACCTGATCACGCACTGGGGAGGGCGGTGCTACTCG TGGGACGTGGTCAACGAGGCGCTGGCGGCGAACGGGTCGTGGGCGTCCAGCATCTG GTACGACACCATCGGGCCCGAGTACTTCTTCCTCGCGTACCGGTTTGCGCAGGAGGC GGTCGAAAAGACCGGCCAGGACATCAAGCTGTACTACAATGACTACGGGATCGAGGCG CCCGGTCCCAAGACGACGGCGGCGTACAACCTGGTCAAGGAGCTGCAGGCGCGAGG CATCCGGATCGATGGCGTGGGGTTGGAGTCGCATTTCGAAGTGGGCGCGACGCCATC CAAGGACGCGCAGGTTGAGGCCAAGCAGGGGTTTTTGGATCTGGGGGTCGATGTTGT CGTCACGGAGCTGGATGTCAGATTCCCGGAGGGGCCGTTCTACACGGCGGCGGGTGA GAAGCAGCAGGCGCAGGACTATTATGATACGGTGGCGAGCTGCGTGGAGGTTGGTCC TCGGTGTGTGGGCATCACGGTGTGGGATTTTGACGATGCGTATTCGTGGGTGCCGTCA TCGTTTCCTGGACAGGGAGCGGCTGATCTGTATAATGGGACGTTGCAGCGGAAGCCG GCGTACTATGCGGTGGCAGAGGCATTGCAGGGGGTGAGTTGTAGTGTGTGCTAA,
or a fragment or variant thereof.

Optionally, the vector comprises the nucleic acid sequence defined in SEQ ID NO:2, or a fragment or variant thereof.

Optionally, the vector comprises the nucleic acid sequence:

ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT

GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAG GCC CAA GAC TAT TAC GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA, or a fragment or variant thereof.

Optionally, the vector comprises the nucleic acid sequence defined in SEQ ID NO:3, or a fragment or variant thereof.

Optionally, the vector further comprises a promoter operatively linked to the nucleic acid sequence:
ATGCGTCTCTCTCCGTCTTTAATAT-
TCGTACCGCTGGTCACACCAGCCTTTACATTGCTAT-
TCAA CTCGAACCTCACATCTCCTCCATGGCTCAAT-
GATCTCGCACAGAGGCGTGGCAAGCTGTGGTTT
GGCACGGCAGCTGA-
CATCCCCGGTCCAGAGCAGCAGGATACGAACTA-
CATGACCATCCTGAAT GATACGAAGATATTTGGG-
GAATTGACGCCTGCGAATTATATGAAGTTCGA
ATACACTGAACCAT CGCCCAATGTCTTCAAC-
TACTCTGGCGGCGACACCATCCTGGC-
CATCGCCGAAAACCACGGCA AGCGCGTTCGCTGC-
CACAACCTCATCTGGGTCAGCCAGCTGCC
CGACTGGGTGGTGAACGGC
AGCTGGACAGCGGCGAGCCTCACAGCGGTGAT-
GAAGACGCACATCACGAACCTGATCACGCA
CTGGGGAGGGCGGTGCTACTCGTGGGACGTGGT-
CAACGAGGCGCTGGCGGCGAACGGGTCG
TGGGCGTCCAGCATCTGGTACGACAC-
CATCGGGCCCGAGTACTTCTTCCTCG
CGTACCGGTTT GCGCAGGAGGCGGTCGAAAA-
GACCGGCCAGGACATCAAGCTGTACTACAATGAC-
TACGGGAT CGAGGCGCCCGGTCCCAA-
GACGACGGCGGCGTACAACCTGGTCAA
GGAGCTGCAGGCGCGA GGCATCCGGATC-
GATGGCGTGGGGTTGGAGTCGCAT-
TTCGAAGTGGGCGCGACGCCATCCAA
GGACGCGCAGGTTGAGGCCAAGCAGGGGTTTTTG-
GATCTGGGGGTCGATGTTGTCGTCACGG AGCTG-
GATGTCAGATTCCCGGAGGGGCCGTTCTA-
CACGGCGGCGGGTGAGAAGCAGCAGGCG
CAGGACTATTATGATACGGTGGCGAGCTGCGTG-
GAGGTTGGTCCTCGGTGTGTGGGCATCACG
GTGTGGGATTTTGACGATGCGTAT-
TCGTGGGTGCCGTCATCGTTTCCTGGACAGG-
GAGCGGCT GATCTGTATAATGGGACGTTGCAGCG-
GAAGCCGGCGTACTATGCGGTGGCAGA
GGCATTGCAG GGGGTGAGTTGTAGTGTGTGCTAA;
or the nucleic acid sequence defined in SEQ ID NO:2; or the nucleic acid sequence defined in SEQ ID NO:3; or the fragment or variant each thereof.

Optionally, the vector further comprises the nucleic acid sequence:

AGCACCACCTACAT-
CATCTCGCCGACGACGTCTGTCG-
GAACGGGCACGACGACCTCGA GCGGCG-
GAAGCGGCGGCACGACTGGCGTGGC
CCAGCATTGGGAGCAGTGCGGTGGA
CTGGGCTGGACTGGTCCGACGG
TTTGCGCAAGTGGCTACACTTGCACTGTCAT-
CAATG AGTATTACTCGCAGTGTCTG or a fragment or variant thereof.

Optionally, the vector comprises the nucleic acid sequence defined in SEQ ID NO:5, or a fragment or variant thereof.

Optionally, the promoter comprises the nucleic acid sequence:

AGATCTAACATCCAAAGACGAAAGGTTGAAT-
GAAACCTTTTTGCCATCCGACATCCACA GGTC-
CATTCTCACACATAAGTGCCAAACGCAACAG-
GAGGGGATACACTAGCAGCAGAC
CGTTGCAAACGCAGGACCTC-
CACTCCTCTTCTCCTCAACACCCACTTTTGC-
CATCGAAA AACCAGCCCAGTTATTGGGCTT-
GATTGGAGCTCGCTCATTCCAATTCC
TTCTATTAGGC TACTAACACCATGACTTTATT-
AGCCTGTCTATCCTGGCCCCCCTGGCGAGGTT-
CATGTT TGTTTAT-
TTCCGAATGCAACAAGCTCCGCATTAC
ACCCGAACATCACTCCAGATGAGGG CTTTCT-
GAGTGTGGGGTCAAATAGTTTCATGTTCCC-
CAAATGGCCCAAAACTGACAGTT
TAAACGCTGTCTTG-
GAACCTAATATGACAAAAGCGTGATCTCATC-
CAAGATGAACTAAG TTTGGTTCGTT-
GAAATGCTAACGGCCAGTTGGTC
AAAAAGAAACTTCCAAAAGTCGGCA
TACCGTTTGTCTTGTTTGGTATTGAT-
TGACGAATGCTCAAAAATAATCTCAT-
TAATGCTTA GCGCAGTCTCTCTATCGCTTCT-
GAACCCCGGTGCACCTGTGCCGAA
ACGCAAATGGGG AAACACCCGCTTTTTGGAT-
GATTATGCATTGTCTCCACATTGTATGCTTC-
CAAGATTCTG GTGGGAATACTGCTGA-
TAGCCTAACGTTCATGATCAAAATTT
AACTGTTCTAACCCCTAC
TTGACAGCAATATATAAACAGAAGG
AAGCTGCCCTGTCTTAAACCTTTTTTTTTAT-
CATC ATTATTAGCTTACTTTCATAAT-
TGCGACTGGTTCCAATTGACAAGCTTTTGAT-
TTTAACGA
CTTTTAACGACAACTTGAGAAGAT-
CAAAAAACAACTAATTATTCGAAACGA, or a fragment or variant thereof.

Optionally, the promoter comprises the nucleic acid sequence defined in SEQ ID NO:4, or a fragment or variant thereof.

According to a fifth aspect of the present invention, there is provided a method of preparing a host cell, the method comprising the steps of:

(a) providing a host cell; and (b) introducing into the host cell a vector comprising the nucleic acid sequence:

ATGCGTCTCTCTCCGTCTTTAATAT-
TCGTACCGCTGGTCACACCAGCCT TTACAT-
TGCTATTCAACTCGAACCTCACATCTCCTC-
CATGGCTCAATGA
TCTCGCACAGAGGCGTGGCAA
GCTGTGGTTTGGCACGGCAGCTGACA
TCCCCGGTCCAGAGCAGCAGGATACGAAC-
TACATGACCATCCTGAATG ATACGAAGATAT-
TTGGGGAATTGACGCCTGCGAATTATAT-
GAAGTTCGA

ATACACTGAACCATCGCCCAATGTCTTCAAC-TACTCTGGCGGCGACAC CATCCTGGC-CATCGCCGAAAAC-CACGGCAAGCGCGTTCGCTGCCACA
ACCTCATCTGGGTCAGCCAGCTGCCCGA CTGGGTGGTGAACGGCAGC
TGGACAGCGGCGAGCCTCACAGCGGTGAT-GAAGACGCACATCACGAA CCTGAT-CACGCACTGGGGAGGGCGGTGC-TACTCGTGGGACGTGGTCA
ACGAGGCGCTGGCGGCGAACGGG
TCGTGGGCGTCCAGCATCTGGTA CGACAC-CATCGGGCCCGAGTACTTCTTCCTCG
CGTACCGGTTTGCGCA
GGAGGCGGTCGAAAAGACCGGCCAGGA-CATCAAGCTGTACTACAATG ACTACGG-GATCGAGGCGCCCGGTCCCAA-GACGACGGCGGCGTACAAC
CTGGTCAAGGAGCTGCAGGCGCGAGG-CATCCGGATCGATGGCGTGG GGTTG-GAGTCGCATTTCGAAGTGGGCGCGACGC-CATCCAAGGACGCG
CAGGTTGAGGCCAAGCAGGGGTTTTTG-GATCTGGGGGTCGATGTTGTC GTCACG-GAGCTGGATGTCAGATTCCCG-GAGGGGCCGTTCTACACGGC
GGCGGGTGAGAAGCAGCAGGCGCAGGACT-ATTATGATACGGTGGCGA GCTGCGTG-GAGGTTGGTCCTCGGTGTGTGGGCAT-CACGGTGTGGGAT
TTTGACGATGCGTATTCGTGGGTGCCGT-CATCGTTTCCTGGACAGGGA GCGGCT-GATCTGTATAATGGGACGTTGCAGCG-GAAGCCGGCGTACTAT
GCGGTGGCAGAGGCATTGCAGGGGGT-GAGTTGTAGTGTGTGCTAA, or a fragment or variant thereof.

Optionally, the vector comprises the nucleic acid sequence defined in SEQ ID NO:2, or a fragment or variant thereof.

Optionally, the vector comprises the nucleic acid sequence:

ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT GGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT GGG GAA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAG GCC CAA GAC TAT TAC GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA, or a fragment or variant thereof.

Optionally, the vector comprises the nucleic acid sequence defined in SEQ ID NO:3, or a fragment or variant thereof.

Optionally, the vector further comprises the nucleic acid sequence:

AGCACCACCTACAT-CATCTCGCCGACGACGTCTGTCG-GAACGGGCACGACGACCTCGA GCGGCG-GAAGCGGCGGCACGACTGGCGTGGCCC AGCATTGGGAGCAGTGCGGTGGA CTGGGCTGGACTGGTCCGACGGTT
TGCGCAAGTGGCTACACTTGCACTGTCAT-CAATG AGTATTACTCGCAGTGTCTG, or a fragment or variant thereof.

Optionally, the vector comprises the nucleic acid sequence defined in SEQ ID NO:5, or a fragment or variant thereof.

Optionally, the vector further comprises a promoter operatively linked to the nucleic acid sequence: ATGCGTCTCTCTCCGTCTTTAATAT-TCGTACCGCTGGTCACACCAGCCTTTACATTGCTAT-TCAA CTCGAACCTCACATCTCCTCCATGGCTCAAT-GATCTCGCACAGAGGCGTGGCAAGCTGTGGTTT GGCACGGCAGCTGA-CATCCCCGGTCCAGAGCAGCAGGATACGAACTA-CATGACCATCCTGAAT GATACGAAGATATTTGGG-GAATTGACGCCTGCGAATTATATGAAGTTC GAATACACTGAACCAT CGCCCAATGTCTTCAAC-TACTCTGGCGGCGACACCATCCTGGC-CATCGCCGAAAACCACGGCA AGCGCGTTCGCTGC-CACAACCTCATCTGGGTCAGCCAGCTG CCCGACTGGGTGGTGAACGGC
AGCTGGACAGCGGCGAGCCTCACAGCGGTGAT-GAAGACGCACATCACGAACCTGATCACGCA CTGGGGAGGGCGGTGCTACTCGTGGGACGTGGT-CAACGAGGCGCTGGCGGCGAACGGGTCG TGGGCGTCCAGCATCTGGTACGACAC-CATCGGGCCCGAGTACTTCTTCCTCGCG TACCGGTTT GCGCAGGAGGCGGTCGAAAA-GACCGGCCAGGACATCAAGCTGTACTACAATGAC-TACGGGAT CGAGGCGCCCGGTCCCAA-GACGACGGCGGCGTACAACCTGGTC AAGGAGCTGCAGGCGCGA GGCATCCGGATC-GATGGCGTGGGGTTGGAGTCGCAT-TTCGAAGTGGGCGCGACGCCATCCAA GGACGCGCAGGTTGAGGCCAAGCAGGGGTTTTTG-GATCTGGGGGTCGATGTTGTCGTCACGG AGCTG-GATGTCAGATTCCCGGAGGGGCCGTTCTA-CACGGCGGCGGGTGAGAAGCAGCAGGCG CAGGACTATTATGATACGGTGGCGAGCTGCGTG-GAGGTTGGTCCTCGGTGTGTGGGCATCACG GTGTGGGATTTTGACGATGCGTAT-TCGTGGGTGCCGTCATCGTTTCCTGGACAGG-GAGCGGCT GATCTGTATAATGGGACGTTGCAGCG- GAAGCCGGCGTACTATGCGGTGGCAGAGGCATTGCAG GGGGTGAGTTGTAGTGTGTGCTAA; or the nucleic acid sequence defined in SEQ ID NO:2; or the nucleic acid sequence defined in SEQ ID NO:3; or the fragment or variant each thereof.

Optionally, the promoter comprises the nucleic acid sequence:

AGATCTAACATCCAAAGACGAAAGGTTGAATGAAACCTTTTTGCCATCCGACATCCACA GGTCCATTCTCACACATAAGTGCCAAACGCAACAGGAGGGGATACACTAGCAGCAGAC CGTTGCAAACGCAGGACCTCCACTCCTCTTCTCCTCAACACCCACTTTTGCCATCGAAA AACCAGCCCAGTTATTGGGCTTGATTGGAGCTCGCTCATTCCAATTC CTTCTATTAGGC TACTAACACCATGACTTTATTAGCCTGTCTATCCTGGCCCCCCTGGCGAGGTTCATGTT TGTTTATTTCCGAATGCAACAAGCTCCGCATTAC ACCCGAACATCACTCCAGATGAGGG CTTTCTGAGTGTGGGGTCAAATAGTTTCATGTTCCCCAAATGGCCCAAAACTGACAGTT TAAACGCTGTCTTGGAACCTAATATGACAAAAGCGTGATCTCATCCAAGATGAACTAAG TTTGGTTCGTTGAAATGCTAACGGCCAGTTGGTCAA AAAGAAACTTCCAAAAGTCGGCA TACCGTTTGTCTTGTTTGGTATTGATTGACGAATGCTCAAAAATAATCTCATTAATGCTTA GCGCAGTCTCTCTATCGCTTCTGAACCCCGGTGCACCTGTGCCGAA ACGCAAATGGGG AAACACCCGCTTTTTGGATGATTATGCATTGTCTCCACATTGTATGCTTCCAAGATTCTG GTGGGAATACTGCTGATAGCCTAACGTTCATGATCAAAATTT AACTGTTCTAACCCCTAC TTGACAGCAATATATAAACAGAAGGAA GCTGCCCTGTCTTAAACCTTTTTTTTATCATC ATTATTAGCTTACTTTCATAATTGCGACTGGTTCCAATTGACAAGCTTTTGATTTTAACGA CTTTTAACGACAACTTGAGAAGATCAAAAAACAACTAATTATTCGAAACGA, or a fragment or variant thereof.

Optionally, the promoter comprises the nucleic acid sequence defined in SEQ ID NO:4, or a fragment or variant thereof.

Optionally, the introducing step (b) comprises transforming, transfecting, or transducing the host cell with the vector. Further optionally, the introducing step (b) comprises transiently transforming, transiently transfecting, or transiently transducing the host cell with the vector. Still further optionally, the introducing step (b) comprises reversibly transforming, reversibly transfecting, or reversibly transducing the host cell with the vector. Still further optionally, the introducing step (b) comprises inducibly transforming, inducibly transfecting, or inducibly transducing the host cell with the vector.

According to a sixth aspect of the present invention, there is provided a method of preparing an isolated polypeptide comprising the amino acid sequence:

MRLSPSLIFVPLVTPAFTLLFNSNLTSPPWLNDLAQRRGKLWFGTAADIPGPEQQDTNYMTI LNDTKIFGELTPANYMKFEYTEPSPNVFNYSGGDTILAIAENHGKRVRCHNLIWVSQLPDWV VNGSWTAASLTAVMKTHITNLITHWGGRCYSWDVVNEALAAN GSWASSIWYDTIGPEYFFL AYRFAQEAVEKTGQDIKLYYNDYGIEAPGPKTTAAYNLVKELQARGIRIDGVGLESHFEVGA TPSKDAQVEAKQGFLDLGVDVVVTELDVRFPEGPFYTAAGEKQQ AQDYYDTVASCVEVGP RCVGITVWDFDDAYSWVPSSFPGQGAADLYNGTLQRKPAYYAVAEALQGVSCSVC, or a fragment or analogue thereof;

the method comprising the steps of:

(a) providing a host cell; and
(b) introducing into the host cell a vector comprising the nucleic acid sequence ATGCGTCTCTCTCCGTCTTTAATATTCGTACCGCTGGTCACACCAGCCT TTACATTGCTATTCAACTCGAACCTCACATCTCCTCCATGGCTCAATGA TCTCGCACAGAGGCGTGGCAAGCTGTG GTTTGGCACGGCAGCTGACA TCCCCGGTCCAGAGCAGCAGGATACGAACTACATGACCATCCTGAATG ATACGAAGATATTTGGGGAATTGACGCCTGCAATTATATGAAGTTCGA ATACACTGAACCATCGCCCAATGTCTTCAACTACTCTGGCGGCGACAC CATCCTGGCCATCGCCGAAAACCACGGCAAGCGCGTTCGCTGCCACA ACCTCATCTGGGTCAGCCAGCTGCCCG ACTGGGTGGTGAACGGCAGC TGGACAGCGGCGAGCCTCACAGCGGTGATGAAGACGCACATCACGAA CCTGATCACGCACTGGGGAGGGCGGTGCTACTCGTGGGACGTGGTCA ACGAGGCGCTGGCGGCGAACGG GTCGTGGGCGTCCAGCATCTGGTA CGACACCATCGGGCCCGAGTACTTCTTCCTC GCGTACCGGTTTGCGCA GGAGGCGGTCGAAAAGACCGGCCAGGACATCAAGCTGTACTACAATG ACTACGGGATCGAGGCGCCCGGTCCCAAGACGACGGCGGCGTACAAC CTGGTCAAGGAGCTGCAGGCGCGAGGCATCCGGATCGATGGCGTGG GGTTGGAGTCGCATTTCGAAGTGGGCGCGACGCCATCCAAGGACGCG CAGGTTGAGGCCAAGCAGGGGTTTTTGGATCTGGGGGTCGATGTTGTC GTCACGGAGCTGGATGTCAGATTCCCGGAGGGGCCGTTCTACACGGC GGCGGGTGAGAAGCAGCAGGCGCAGGACTATTATGATACGGTGGCGA GCTGCGTGGAGGTTGGTCCTCGGTGTGTGGGCATCACGGTGTGGAT TTTGACGATGCGTATTCGTGGGTGCCGTCATCGTTTCCTGGACAGGGA GCGGCTGATCTGTATAATGGGACGTTGCAGCGGAAGCCGGCGTACTAT GCGGTGGCAGAGGCATTGCAGGGGGTGAGTTGTAGTGTGTGCTAA, or
a fragment or variant thereof;

(c) transcribing the vector to obtain a ribonucleic acid; and
(d) translating the ribonucleic acid to obtain the isolated polypeptide.

Optionally, the isolated polypeptide comprises the amino acid sequence defined in SEQ ID NO:1, or a fragment or analogue thereof.

Optionally, the vector comprises the nucleic acid sequence defined in SEQ ID NO:2, or a fragment or variant thereof.

Optionally, the vector comprises the nucleic acid sequence:
ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAG GCC CAA GAC TAT TAC GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA,
or a fragment or variant thereof.

Optionally, the vector comprises the nucleic acid sequence defined in SEQ ID NO:3, or a fragment or variant thereof.

Optionally, the vector further comprises the nucleic acid sequence:
AGCACCACCTACAT-CATCTCGCCGACGACGTCTGTCG-GAACGGGCACGACGACCTCGA GCGGCG-GAAGCGGCGGCACGACTGGCGTGGCCC AGCATTGGGAGCAGTGCGGTGGA CTGGGCTGGACTGGTCCGACGGTTTGCGC AAGTGGCTACACTTGCACTGTCATCAATG AGT-ATTACTCGCAGTGTCTG
or a fragment or variant thereof.

Optionally, the vector comprises the nucleic acid sequence defined in SEQ ID NO:5, or a fragment or variant thereof.

Optionally, the vector further comprises a promoter operatively linked to the nucleic acid sequence:
ATGCGTCTCTCTCCGTCTTTAATAT-TCGTACCGCTGGTCACACCAGCCTTTACATTGCTAT-TCAA CTCGAACCTCACATCTCCTCCATGGCTCAAT-GATCTCGCACAGAGGCGTGGCAAGCTGTGGTTT GGCACGGCAGCTGA-CATCCCCGGTCCAGAGCAGCAGGATACGAACTA-CATGACCATCCTGAAT GATACGAAGATATTTGGG-GAATTGACGCCTGCGAATTATATGAAGTTCGA ATACACTGAACCAT CGCCCAATGTCTTCAAC-TACTCTGGCGGCGACACCATCCTGGC-CATCGCCGAAAACCACGGCA AGCGCGTTCGCTGC-CACAACCTCATCTGGGTCAGCCAGCTGC CCGACTGGGTGGTGAACGGC AGCTGGACAGCGGCGAGCCTCACAGCGGTGAT-GAAGACGCACATCACGAACCTGATCACGCA CTGGGGAGGGCGGTGCTACTCGTGGGACGTGGT-CAACGAGGCGCTGGCGGCGAACGGGTCG TGGGCGTCCAGCATCTGGTACGACAC-CATCGGGCCCGAGTACTTCTTCCTCGCGTACC GGTTT GCGCAGGAGGCGGTCGAAAA-GACCGGCCAGGACATCAAGCTGTACTACAATGAC-TACGGGAT CGAGGCGCCCGGTCCCAA-GACGACGGCGGCGTACAACCTGGTCAAGGAG CTGCAGGCGCGA GGCATCCGGATC-GATGGCGTGGGGTTGGAGTCGCAT-TTCGAAGTGGGCGCGACGCCATCCAA GGACGCGCAGGTTGAGGCCAAGCAGGGGTTTTTG-GATCTGGGGGTCGATGTTGTCGTCACGG AGCTG-GATGTCAGATTCCCGGAGGGGCCGTTCTA-CACGGCGGCGGGTGAAGCAGCAGGCG CAGGACTATTATGATACGGTGGCGAGCTGCGTG-GAGGTTGGTCCTCGGTGTGTGGGCATCACG GTGTGGGATTTTGACGATGCGTAT-TCGTGGGTGCCGTCATCGTTTCCTGGACAGG-GAGCGGCT GATCTGTATAATGGGACGTTGCAGCG-GAAGCCGGCGTACTATGCGGTGGCAGAGG CATTGCAG GGGGTGAGTTGTAGTGTGTGCTAA; or the nucleic acid sequence defined in SEQ ID NO:2; or the nucleic acid sequence defined in SEQ ID NO:3; or the fragment or variant each thereof.

Optionally, the promoter comprises the nucleic acid sequence:
AGATCTAACATCCAAAGACGAAAGGTTGAAT-GAAACCTTTTTGCCATCCGACATCCACA GGTC-CATTCTCACACATAAGTGCCAAACGCAACAG-GAGGGGATACACTAGCAGCAGAC CGTTGCAAACGCAGGACCTC-CACTCCTCTTCTCCTCAACACCCACTTTTGC-CATCGAAA AACCAGCCCAGTTATTGGGCTT-GATTGGAGCTCGCTCATTCCAAT TCCTTCTATTAGGC TACTAACACCATGACTTT-ATTAGCCTGTC-TATCCTGGCCCCCTGGCGAGGTTCATGTT TGTTTATTTCCGAATGCAACAAGCTCCGCAT-TACACCCGAACATCACTCCAGATGAGGG CTTTCTGAGTGTGGGGTCAAATAGTTT-CATGTTCCCCAAATGGCCCAAAACTGACAGTT TAAACGCTGTCTTG-GAACCTAATATGACAAAAGCGTGATCTCATC-CAAGATGAACTAAG TTTGGTTCGTT-GAAATGCTAACGGCCAGTTGGTCAAAAAG AAACTTCCAAAAGTCGGCA TACCGTTTGTCTTGTTTGGTATTGAT-TGACGAATGCTCAAAAATAATCTCAT-TAATGCTTA GCGCAGTCTCTCTATCGCTTCT-GAACCCCGGTGCACCTGTGCCGAAACG CAAATGGGG AAACACCCGCTTTTTGGATGAT-TATGCATTGTCTCCACATTGTATGCTTCCAA-GATTCTG GTGGGAATACTGCTGA-TAGCCTAACGTTCATGATCAAAATTTA ACTGTTCTAACCCCTAC TTGACAGCAATATATAAACAGAAGGAAGC TGCCCTGTCTTAAACCTTTTTTTTTATCATCATT-
ATTAGCTTACTTTCATAATTGCGACTGGTTC-
CAATTGACAAGCTTTTGATTTTAACGA CTTT-
TAACGACAACTTGAGAAGATCAAAAAACA
ACTAATTATTCGAAACGA,
or a fragment or variant thereof.

Optionally, the promoter comprises the nucleic acid sequence defined in SEQ ID NO:4, or a fragment or variant thereof.

According to a seventh aspect of the present invention, there is provided a method of degrading lignocellulose biomass, the method comprising the steps of:
(a) providing a lignocellulose biomass; and
(b) contacting the lignocellulose biomass with an isolated polypeptide comprising the amino acid sequence:
MRLSPSLIFVPLVTPAFTLLFNSNLTSPPWLND-
LAQRRGKLWFGTAADIPG PEQQDTNYM-
TILNDTKIFGELTPANYMKFEYTEPSPNVF-
NYSGGDTILAIAE
NHGKRVRCHNLIWVSQLPDWVVNG-
SWTAASLTAVMKTHITNLITHWGGR
CYSWDVVNEALAANGSWASSIWYDTIGPEYF-
FLAYRFAQEAVEKTGQDIK LYYNDY-
GIEAPGPKTTAAYNLVKELQARGIRIDGV-
GLESHFEVGATPSKDA
QVEAKQGFLD-
LGVDVVVTELDVRFPEGPFYTAAGEKQQ
AQDYYDTVASC VEVGPRCVGITVWDFDDAY-
SWVPSSFPGQGAADLYNGTLQRKPAYYAVA
EALQGVSCSVC, or a fragment or analogue thereof.

Optionally, the isolated polypeptide comprises the amino acid sequence defined in SEQ ID NO:1, or a fragment or analogue thereof.

Optionally, the isolated polypeptide is encoded by a polynucleotide comprising the nucleic acid sequence:
ATGCGTCTCTCTCCGTCTTTAATAT-
TCGTACCGCTGGTCACACCAGCCTTTACAT-
TGCTA TTCAACTCGAACCTCACATCTCCTC-
CATGGCTCAATGATCTCGCACAGAGGCG
TGGCAA GCTGTGGTTTGGCACGGCAGCTGA-
CATCCCCGGTCCAGAGCAGCAGGA-
TACGAACTA CATGACCATCCTGAATGA-
TACGAAGATATTTGGGGAATTGACGCC
TGCGAATTATATGA AGTTCGAATACACTGAAC-
CATCGCCCAATGTCTTCAAC-
TACTCTGGCGGCGACACCATC CTGGC-
CATCGCCGAAAACCACGGCAAGCGCG
TTCGCTGCCACAACCTCATCTGGGTCA
GCCAGCTGCCCGACTGGGTGGT-
GAACGGCAGCTGGACAGCGGCGAGCCT-
CACAGCG GTGATGAAGACGCACAT-
CACGAACCTGATCACGCACTGGGGAG
GGCGGTGCTACTCG TGGGACGTGGT-
CAACGAGGCGCTGGCGGCGAACGGGTCGT
GGGCGTCCAGCATCTG GTACGACAC-
CATCGGGCCCGAGTACTTCTTCCTCGCG
TACCGGTTTGCGCAGGAGGC GGTCGAAAA-
GACCGGCCAGGACATCAAGCTGTACTA-
CAATGACTACGGGATCGAGGCG CCCGGTCC-
CAAGACGACGGCGGCGTACAACCTGGTC
AAGGAGCTGCAGGCGCGAGG CATCCGGATC-
GATGGCGTGGGGTTGGAGTCGCAT-
TTCGAAGTGGGCGCGACGCCATC
CAAGGACGCGCAGGTTGAGGC-
CAAGCAGGGGTTTTTGGATCTGGGGGTC-
GATGTTGT CGTCACGGAGCTGGATGTCAGAT-
TCCCGGAGGGGCCGTTCTACACGGCGGCGGGT-
GA
GAAGCAGCAGGCGCAGGACTATTATGA-
TACGGTGGCGAGCTGCGTGGAGGTTGGTCC
TCGGTGTGTGGGCATCACGGTGTGGGAT-
TTTGACGATGCGTATTCGTGGGTGCCGTCA
TCGTTTCCTGGACAGGGAGCGGCT-
GATCTGTATAATGGGACGTTGCAGCG-
GAAGCCG GCGTACTATGCGGTGGCAGAGG-
CATTGCAGGGGGTGAGTTGTAGTGTGTGCTAA,
or a fragment or variant thereof.

Optionally, the isolated polypeptide is encoded by a polynucleotide comprising the nucleic acid sequence defined in SEQ ID NO:2, or a fragment or variant thereof.

Optionally, the isolated polypeptide is encoded by a polynucleotide comprising the nucleic acid sequence:
ATG AGG CTG TCA CCA TCC CTA ATA TTC GTA
CCT CTT GTG ACA CCC GCT TTC ACC TTA CTG
TTC AAT TCC AAC CTA ACG TCC CCC CCT TGG
CTT AAT GAT CTG GCA CAG AGG AGG GGT AAG
TTA TGG TTT GGT ACC GCC GCA GAT ATT CCC
GGT CCT GAG CAA CAA GAC ACA AAC TAT ATG
ACG ATA CTT AAT GAT ACA AAG ATT TTC GGA
GAA CTA ACT CCA GCC AAC TAC ATG AAA TTT
GAG TAC ACG GAG CCC AGT CCC AAT GTC TTC
AAT TAC AGT GGC GGT GAT ACT ATT CTG GCA
ATT GCA GAA AAT CAT GGT AAA AGG GTT AGG
TGT CAT AAT CTT ATT TGG GTT TCA CAA CTT
CCC GAT TGG GTT GTG AAC GGT TCT TGG ACT
GCC GCT TCC CTA ACT GCT GTA ATG AAG ACA
CAT ATT ACG AAT TTA ATC ACA CAT TGG GGA
GGT CGT TGT TAC AGT TGG GAT GTC GTT AAC
GAA GCT CTG GCA GCC AAC GGT TCA TGG
GCT AGT TCA ATC TGG TAC GAC ACC ATA GGA
CCA GAG TAT TTC TTC CTA GCA TAC AGA TTC
GCT CAG GAG GCT GTT GAG AAA ACC GGC
CAA GAT ATC AAA TTG TAC TAT AAC GAC TAT
GGC ATT GAA GCT CCT GGT CCC AAG ACA ACT
GCA GCC TAT AAT CTG GTC AAG GAA CTT CAA
GCA AGA GGA ATC CGT ATC GAC GGC GTC GGT
TTG GAG TCT CAT TTT GAG GTG GGA GCA ACC
CCT TCC AAG GAT GCT CAG GTT GAA GCT AAA
CAA GGT TTT CTT GAC CTG GGA GTA GAC GTT
GTC GTT ACG GAG TTG GAT GTC CGT TTC CCC
GAG GGC CCT TTT TAC ACC GCA GCT GGA
GAG AAG CAA CAG GCC CAA GAC TAT TAC
GAC ACA GTT GCA AGT TGC GTA GAA GTC GGC
CCC AGG TGC GTG GGC ATT ACT GTC TGG GAC
TTC GAC GAC GCT TAC TCT TGG GTC CCT TCC
TCC TTT CCC GGC CAA GGT GCC GCA GAC CTA
TAC AAT GGT ACT TTA CAG AGG AAG CCT GCT
TAC TAT GCT GTG GCA GAG GCA CTA CAA GGC
GTG TCA TGC AGT GTC TGC TAA,
or a fragment or variant thereof.

Optionally, the isolated polypeptide is encoded by a polynucleotide comprising the nucleic acid sequence defined in SEQ ID NO:3, or a fragment or variant thereof.

Optionally, the contacting step (b) comprises contacting the lignocellulose biomass with a host cell comprising a vector comprising the nucleic acid sequence:
ATGCGTCTCTCTCCGTCTTTAATAT-
TCGTACCGCTGGTCACACCAGCCTTTACAT-
TGCTA TTCAACTCGAACCTCACA
TCTCCTCCATGGCTCAAT-
GATCTCGCACAGAGGCGTGGCAA
GCTGTGGTTTGGCACGGCAGCTGA-
CATCCCCGGTCCAGAGCAGCAGGA- TACGAACTA CATGACCATCCTGAATGA-
TACGAAGATATTTGGGGAATTGACGCCT
GCGAATTATATGA AGTTCGAATACACTGAAC-
CATCGCCCAATGTCTTCAAC-
TACTCTGGCGGCGACACCATC CTGGC-
CATCGCCGAAAACCACGGCAAGCGCGT
TCGCTGCCACAACCTCATCTGGGTCA
GCCAGCTGCCCGACTGGGTGGT-
GAACGGCAGCTGGACAGCGGCGAGCCT-
CACAGCG GTGATGAAGACGCACAT-
CACGAACCTGATCACGCACTGGGGAGG
GCGGTGCTACTCG TGGGACGTGGT-
CAACGAGGCGCTGGCGGCGAACGGG
TCGTGGGCGTCCAGCATCTG GTACGACAC-
CATCGGGCCCGAGTACTTCTTCCTCGC
GTACCGGTTTGCGCAGGAGGC GGTCGAAAA-
GACCGGCCAGGACATCAAGCTGTACTA-
CAATGACTACGGGATCGAGGCG CCCGGTCC-
CAAGACGACGGCGGCGTACAACCT
GGTCAAGGAGCTGCAGGCGCGAGG CATCCG-
GATCGATGGCGTGGGGTTGGAGTCGCAT-
TCGAAGTGGGCGCGACGCCATC
CAAGGACGCGCAGGTTGAGGC-
CAAGCAGGGGTTTTTGGATCTGGGGGTC-
GATGTTGT CGTCACGGAGCTGGATGTCAGAT-
TCCCGGAGGGGCCGTTCTACACGGCGGCGGGT-
GA
GAAGCAGCAGGCGCAGGACTATTATGA-
TACGGTGGCGAGCTGCGTGGAGGTTGGTCC
TCGGTGTGTGGGCATCACGGTGTGGGAT-
TTTGACGATGCGTATTCGTGGGTGCCGTCA
TCGTTTCCTGGACAGGGAGCGGCT-
GATCTGTATAATGGGACGTTGCAGCG-
GAAGCCG GCGTACTATGCGGTGGCAGAGG-
CATTGCAGGGGGTGAGTTGTAGTGTGTGCTAA,
or a fragment or variant thereof.

Optionally, the vector comprises the nucleic acid sequence defined in SEQ ID NO:2, or a fragment or variant thereof.

Optionally, the vector comprises the nucleic acid sequence:

ATG AGG CTG TCA CCA TCC CTA ATA TTC GTA
CCT CTT GTG ACA CCC GCT TTC ACC TTA CTG
TTC AAT TCC AAC CTA ACG TCC CCC CCT TGG
CTT AAT GAT CTG GCA CAG AGG AGG GGT AAG
TTA TGG TTT GGT ACC GCC GCA GAT ATT CCC
GGT CCT GAG CAA CAA GAC ACA AAC TAT ATG
ACG ATA CTT AAT GAT ACA AAG ATT TTC GGA
GAA CTA ACT CCA GCC AAC TAC ATG AAA TTT
GAG TAC ACG GAG CCC AGT CCC AAT GTC TTC
AAT TAC AGT GGC GGT GAT ACT ATT CTG GCA
ATT GCA GAA AAT CAT GGT AAA AGG GTT AGG
TGT CAT AAT CTT ATT TGG GTT TCA CAA CTT
CCC GAT TGG GTT GTG AAC GGT TCT TGG ACT
GCC GCT TCC CTA ACT GCT GTA ATG AAG ACA
CAT ATT ACG AAT TTA ATC ACA CAT TGG GGA
GGT CGT TGT TAC AGT TGG GAT GTC GTT AAC
GAA GCT CTG GCA GCC AAC GGT TCA TGG
GCT AGT TCA ATC TGG TAC GAC ACC ATA GGA
CCA GAG TAT TTC TTC CTA GCA TAC AGA TTC
GCT CAG GAG GCT GTT GAG AAA ACC GGC
CAA GAT ATC AAA TTG TAC TAT AAC GAC TAT
GGC ATT GAA GCT CCT GGT CCC AAG ACA ACT
GCA GCC TAT AAT CTG GTC AAG GAA CTT CAA
GCA AGA GGA ATC CGT ATC GAC GGC GTC GGT
TTG GAG TCT CAT TTT GAG GTG GGA GCA ACC
CCT TCC AAG GAT GCT CAG GTT GAA GCT AAA
CAA GGT TTT CTT GAC CTG GGA GTA GAC GTT
GTC GTT ACG GAG TTG GAT GTC CGT TTC CCC
GAG GGC CCT TTT TAC ACC GCA GCT GGA
GAG AAG CAA CAG GCC CAA GAC TAT TAC
GAC ACA GTT GCA AGT TGC GTA GAA GTC GGC
CCC AGG TGC GTG GGC ATT ACT GTC TGG GAC
TTC GAC GAC GCT TAC TCT TGG GTC CCT TCC
TCC TTT CCC GGC CAA GGT GCC GCA GAC CTA
TAC AAT GGT ACT TTA CAG AGG AAG CCT GCT
TAC TAT GCT GTG GCA GAG GCA CTA CAA GGC
GTG TCA TGC AGT GTC TGC TAA,
or a fragment or variant thereof.

Optionally, the vector comprises the nucleic acid sequence defined in SEQ ID NO:3, or a fragment or variant thereof.

Optionally, the vector further comprises the nucleic acid sequence:

AGCACCACCTACAT-
CATCTCGCCGACGACGTCTGTCG-
GAACGGGCACGACGACCTCGA GCGGCG-
GAAGCGGCGGCACGACTGGCGTGGCCC
AGCATTGGGAGCAGTGCGGTGGA
CTGGGCTGGACTGGTCCGACGGT
TTGGCCAAGTGGCTACACTTGCACTGTCAT-
CAATG AGTATTACTCGCAGTGTCTG or a fragment or variant thereof.

Optionally, the vector comprises the nucleic acid sequence defined in SEQ ID NO:5, or a fragment or variant thereof.

Optionally, the vector further comprises a promoter operatively linked to the nucleic acid sequence:
ATGCGTCTCTCTCCGTCTTTAATAT-
TCGTACCGCTGGTCACACCAGCCTTTACATTGCTAT-
TCAA CTCGAACCTCACATCTCCTCCATGGCTCAAT-
GATCTCGCACAGAGGCGTGGCAAGCTGTGGTTT
GGCACGGCAGCTGA-
CATCCCCGGTCCAGAGCAGCAGGATACGAACTA-
CATGACCATCCTGAAT GATACGAAGATATTTGGG-
GAATTGACGCCTGCGAATTATATGAA
GTTCGAATACACTGAACCAT CGCCCAATGTCTT-
CAACTACTCTGGCGGCGACACCATCCTGGC-
CATCGCCGAAAACCACGGCA AGCGCGTTCGCTGC-
CACAACCTCATCTGGGTCAGCCAGCTGC
CCGACTGGGTGGTGAACGGC
AGCTGGACAGCGGCGAGCCTCACAGCGGTGAT-
GAAGACGCACATCACGAACCTGATCACGCA
CTGGGGAGGCGGTGCTACTCGTGGGACGTGGT-
CAACGAGGCGCTGGCGGCGAACGGGTCG
TGGGCGTCCAGCATCTGGTACGACAC-
CATCGGGCCCGAGTACTTCTTCCTCGCGTAC
CGGTTT GCGCAGGAGGCGGTCGAAAA-
GACCGGCCAGGACATCAAGCTGTACTACAATGAC-
TACGGGAT CGAGGCGCCCGGTCCCAA-
GACGACGGCGGCGTACAACCTGGTCAAGGA
GCTGCAGGCGCGA GGCATCCGGATC-
GATGGCGTGGGGTTGGAGTCGCAT-
TCGAAGTGGGCGCGACGCCATCCAA
GGACGCGCAGGTTGAGGCCAAGCAGGGGTTTTTG-
GATCTGGGGGTCGATGTTGTCGTCACGG AGCTG-
GATGTCAGATTCCCGGAGGGGCCGTTCTA-
CACGGCGGCGGGTGAGAAGCAGCAGGCG
CAGGACTATTATGATACGGTGGCGAGCTGCGTG-
GAGGTTGGTCCTCGGTGTGTGGGCATCACG
GTGTGGGATTTTGACGATGCGTAT-
TCGTGGGTGCCGTCATCGTTTCCTGGACAGG-
GAGCGGCT GATCTGTATAATGGGACGTTGCAGCG-
GAAGCCGGCGTACTATGCGGTGGCA GAGGCATTGCAG GGGGTGAGTTGTAGTGTGTGCTAA; or the nucleic acid sequence defined in SEQ ID NO:2; or the nucleic acid sequence defined in SEQ ID NO:3; or the fragment or variant each thereof.

Optionally, the promoter comprises the nucleic acid sequence:

AGATCTAACATCCAAAGACGAAAGGTTGAATGAAACCTTTTTGCCATCCGACATCCACA GGTCCATTCTCACACATAAGTGCCAAACGCAACAGGAGGGGATACACTAGCAGCAGAC CGTTGCAAACGCAGGACCTCCACTCCTCTTCTCCTCAACACCCACTTTTGCCATCGAAA AACCAGCCCAGTTATTGGGCTTGATTGGAGCTCGCTCATTCCAATTCCTTCTA TTAGGC TACTAACACCATGACTTTATTAGCCTGTCTATCCTGGCCCCCCTGGCGAGGTTCATGTT TGTTTATTTCCGAATGCAACAAGCTCCGCATTACAC CCGAACATCACTCCAGATGAGGG CTTTCTGAGTGTGGGGTCAAATAGTTTCATGTTCCCCAAATGGCCCAAAACTGACAGTT TAAACGCTGTCTTGGAACCTAATATGACAAAAGCGTGATCTCATCCAAGATGAACTAAG TTTGGTTCGTTGAAATGCTAACGGCCAGTTGGTCAAAAA GAAACTTCCAAAAGTCGGCA TACCGTTTGTCTTGTTTGGTATTGATTGACGAATGCTCAAAAATAATCTCATTAATGCTTA GCGCAGTCTCTCTATCGCTTCTGAACCCCGGTGCACCTGTGCCGAAACG CAAATGGGG AAACACCCGCTTTTTGGATGATTATGCATTGTCTCCACATTGTATGCTTCCAAGATTCTG GTGGGAATACTGCTGATAGCCTAACGTTCATGATCAAAATTTAAC TGTTCTAACCCCTAC TTGACAGCAATATATAAACAGAAGGAA GCTGCCCTGTCTTAAACCTTTTTTTTATCATC ATTATTAGCTTACTTTCATAATTGCGACTGGTTCCAATTGACAAGCTTTTGATTTTAACGA CTTTTAACGACAACTTGAGAAGATCAAAAAACAACTAATTATTCGAAACGA, or a fragment or variant thereof.

Optionally, the promoter comprises the nucleic acid sequence defined in SEQ ID NO:4, or a fragment or variant thereof.

Optionally, the isolated polypeptide or fragment or analogue thereof is, or is derived from, a fungal polypeptide.

Further optionally, the isolated polypeptide or fragment or analogue thereof is, or is derived from, a Trichocomaceae fungal family polypeptide.

Still further optionally, the isolated polypeptide or fragment or analogue thereof is, or is derived from, a *Rasamsonia* polypeptide. Still further optionally, the isolated polypeptide or fragment or analogue thereof is, or is derived from, a *Rasamsonia aegroticola* polypeptide, a *Rasamsonia argillacea* polypeptide, a *Rasamsonia brevistipitata* polypeptide, a *Rasamsonia byssochlamydoides* polypeptide, a *Rasamsonia columbiensis* polypeptide, a *Rasamsonia composticola* polypeptide, a *Rasamsonia cylindrospora* polypeptide, a *Rasamsonia eburnean* polypeptide, a *Rasamsonia emersonii* polypeptide, a *Rasamsonia piperina* polypeptide, and a *Rasamsonia pulvericola* polypeptide. Still further optionally, the isolated polypeptide or fragment or analogue thereof is, or is derived from, a *R. emersonii* polypeptide.

Still further optionally, the isolated polypeptide or fragment or analogue thereof is, or is derived, from *R. emersonii*, wherein the *R. emersonii* strain is selected from a strain of *R. emersonii* deposited under one of the following biological depositary numbers or having one of the following names: ATCC 16479, CBS 393.64, CECT 2607, DTO 4811, IFO 31232, IBT 31218, IBT 21695, IMI 116815, IMI 116815ii, NRRL 3221, MycoBank 339920, *Penicillium emersonii*, *Penicillium* sp. *emersonii*, *Rasamsonia emersonii* (Stolk) Houbraken & Frisvad 2012, *Talaromyces emersonii* Stolk 1965, *Rasamsonia emersonii* (Stolk) Houbraken & Frisvad, Antonie van Leeuwenhoek 101, and *Talaromyces emersonii* Stolk, Antonie van Leeuwenhoek 31 (3): 262 (1965).

Still further optionally, the isolated polypeptide or fragment or analogue thereof is, or is derived, from *R. emersonii*, wherein the *R. emersonii* strain is IMI 116815.

Optionally, the isolated polypeptide or fragment or analogue thereof has xylanase activity. Further optionally, the isolated polypeptide or fragment or analogue thereof has endo-(1→4)-beta-xylan 4-xylanohydrolase activity.

Optionally or additionally, the isolated polypeptide or fragment or analogue thereof has limited or no cellulase activity. Further optionally or additionally, the isolated polypeptide or fragment or analogue thereof has no or limited endo-1,4-beta-D-glucanase activity. Still further optionally or additionally, the isolated polypeptide or fragment or analogue thereof has limited or no carboxymethyl cellulase (CMCase), avicelase, celludextrinase, cellulase A, cellulosin AP, alkali cellulase, cellulase A 3, 9.5 cellulase, or pancellase SS activity.

Optionally or additionally, the isolated polypeptide or fragment or analogue thereof has at least one of xylan from beechwood degradation activity, azo-wheatarabinoxylan degradation activity, wheatarabinoxylan degradation activity, xylopranoside degradation activity and p-nitrophenyl xylopranoside degradation activity.

Optionally, the isolated polypeptide or fragment or analogue thereof has greater xylan from beechwood degradation activity than any one of xylan from beechwood degradation activity, azo-wheatarabinoxylan degradation activity, wheatarabinoxylan degradation activity, xylopranoside degradation activity and p-nitrophenyl xylopranoside degradation activity.

Further optionally, the isolated polypeptide or fragment or analogue thereof has greater xylan from beechwood degradation activity than wheatarabinoxylan degradation activity.

Optionally, the isolated polypeptide or fragment or analogue thereof has a molecular weight of at least 48.1 kDa. Further optionally, the isolated polypeptide or fragment or analogue thereof has a molecular weight of at least 50.1 kDa. Still further optionally, the isolated polypeptide or fragment or analogue thereof has a molecular weight of 50.1-81.9 kDa.

Optionally, the isolated polypeptide fragment has a molecular weight of at least 1.0 kDa. Further optionally, the isolated polypeptide fragment has a molecular weight of at least 2.5 kDa. Still further optionally, the isolated polypeptide fragment has a molecular weight of at least 6.5 kDa. Still further optionally, the isolated polypeptide fragment has a molecular weight of at least 13.0 kDa. Still further optionally, the isolated polypeptide fragment has a molecular weight of at least 26.5 kDa. Still further optionally, the isolated polypeptide fragment has a molecular weight of at least 40.0 kDa. Still further optionally, the isolated polypeptide fragment has a molecular weight of at least 45.0 kDa. Still further optionally, the isolated polypeptide fragment has a molecular weight of at least 47.5 kDa. Still further optionally, the isolated polypeptide fragment has a molecular weight of at least 48.1 kDa. Still further optionally, the isolated polypeptide fragment has a molecular weight of at least 50.0 kDa. Still further optionally, the isolated polypeptide fragment has a molecular weight of at least 50.1 kDa. Still further optionally, the isolated polypeptide fragment has a molecular weight of at least 52.5 kDa. Still further optionally, the isolated polypeptide fragment has a molecular weight of at least 55.0 kDa. Still further optionally, the isolated polypeptide fragment has a molecular weight of at least 65.0 kDa. Still further optionally, the isolated polypeptide fragment has a molecular weight of at least 70.0 kDa. Still further optionally, the isolated polypeptide fragment has a molecular weight of at least 75.0 kDa. Still further optionally, the isolated polypeptide fragment has a molecular weight of at least 80.0 kDa. Still further optionally, the isolated polypeptide fragment has a molecular weight of at least 81.9 kDa. Still further optionally, the isolated polypeptide fragment has a molecular weight of at least 82.0 kDa.

Optionally, the isolated polypeptide fragment is at least 10 amino acids in length. Further optionally, the isolated polypeptide fragment is at least 20 amino acids in length. Still further optionally, the isolated polypeptide fragment is at least 50 amino acids in length. Still further optionally, the isolated polypeptide fragment is at least 100 amino acids in length. Still further optionally, the isolated polypeptide fragment is at least 200 amino acids in length. Still further optionally, the isolated polypeptide fragment is at least 300 amino acids in length. Still further optionally, the isolated polypeptide fragment is at least 362 amino acids in length. Still further optionally, the isolated polypeptide fragment is 362 amino acids in length.

Optionally, the isolated polypeptide fragment is at least 10 amino acids in length comprising at least amino acid residues 265-275 of the amino acid sequence:
MRLSPSLIFVPLVTPAFTLLFNSNLTSPPWLND-LAQRRGKLWFGTAADIPGPEQQDTNYMTI LNDTKIFGELTPANYMKFEYTEPSPNVF-NYSGGDTILAIAENHGKRVRCHN-LIWVSQLPDWV VNGSWTAASLTAVMKTHITN-LITHWGGRCYSWDVVNEALAANGSWA SSIWYDTIGPEYFFL AYRFAQEAVEKTGQDIK-LYYNDYGIEAPGPKTTAAYNLVKELQAR-GIRIDGVGLESHFEVGA TPSKDAQVEAKQGFLD-LGVDVVVTELDVRFPEGPFYTAAGEKQ QAQDYYDTVASCVEVGP RCVGITVWDFDDAY-SWVPSSFPGQGAADLYNGTLQRKPAYYA-VAEALQGVSCSVC,
or an analogue thereof.

Further optionally, the isolated polypeptide fragment is at least 10 amino acids in length comprising at least amino acid residues 265-275 of the amino acid sequence defined in SEQ ID NO:1, or an analogue thereof.

Optionally or additionally, the isolated polypeptide fragment is at least 18 amino acids in length comprising at least amino acid residues 1-18 of the amino acid sequence:
MRLSPSLIFVPLVTPAFTLLFNSNLTSPPWLND-LAQRRGKLWFGTAADIPGPEQQDTNYMTI LNDTKIFGELTPANYMKFEYTEPSPNVF-NYSGGDTILAIAENHGKRVRCHN-LIWVSQLPDWV VNGSWTAASLTAVMKTHITN-LITHWGGRCYSWDVVNEALAANGSW ASSIWYDTIGPEYFFL AYRFAQEAVEKTGQDIK-LYYNDYGIEAPGPKTTAAYNLVKELQAR-GIRIDGVGLESHFEVGA TPSKDAQVEAKQGFLD-LGVDVVVTELDVRFPEGPFYTAAGEKQ QAQDYYDTVASCVEVGP RCVGITVWDFDDAY-SWVPSSFPGQGAADLYNGTLQRKPAYYA-VAEALQGVSCSVC,
or an analogue thereof.

Further optionally or additionally, the isolated polypeptide fragment is at least 18 amino acids in length comprising at least amino acid residues 1-18 of the amino acid sequence defined in SEQ ID NO:1, or an analogue thereof.

Optionally or additionally, the isolated polypeptide fragment is at least 344 amino acids in length comprising at least amino acid residues 19-362 of the amino acid sequence:
MRLSPSLIFVPLVTPAFTLLFNSNLTSPPWLND-LAQRRGKLWFGTAADIPGPEQQDTNYMTI LNDTKIFGELTPANYMKFEYTEPSPNVF-NYSGGDTILAIAENHGKRVRCHN-LIWVSQLPDWV VNGSWTAASLTAVMKTHITN-LITHWGGRCYSWDVVNEALAANGSWAS SIWYDTIGPEYFFL AYRFAQEAVEKTGQDIK-LYYNDYGIEAPGPKTTAAYNLVKELQAR-GIRIDGVGLESHFEVGA TPSKDAQVEAKQGFLD-LGVDVVVTELDVRFPEGPFYTAAGEKQQ AQDYYDTVASCVEVGP RCVGITVWDFDDAY-SWVPSSFPGQGAADLYNGTLQRKPAYYA-VAEALQGVSCSVC,
or an analogue thereof.

Further optionally or additionally, the isolated polypeptide fragment is at least 344 amino acids in length comprising at least amino acid residues 19-362 of the amino acid sequence defined in SEQ ID NO:1, or an analogue thereof.

Optionally, the isolated polypeptide analogue has at least 70% sequence identity to the amino acid sequence:
MRLSPSLIFVPLVTPAFTLLFNSNLTSPPWLND-LAQRRGKLWFGTAADIPGPEQQDTNYMTI LNDTKIFGELTPANYMKFEYTEPSPNVF-NYSGGDTILAIAENHGKRVRCHN-LIWVSQLPDWV VNGSWTAASLTAVMK THITNLITHWGGRCYSWDVVNEALAANGSWAS-SIWYDTIGPEYFFL AYRFAQEAVEKTGQDIK-LYYNDYGIEAPGPKTTAAYNLVKELQAR-GIRIDGVGLESHFEVGA TPSKDAQVEAKQGFLD-LGVDVVVTELDVRFPEGPFYTAAGEKQQA QDYYDTVASCVEVGP RCVGITVWDFDDAY-SWVPSSFPGQGAADLYNGTLQRKPAYYA-VAEALQGVSCSVC,
or a fragment thereof.

Optionally, the isolated polypeptide analogue has at least 70% sequence identity to the amino acid sequence defined in SEQ ID NO:1, or a fragment thereof.

Optionally, the isolated polypeptide analogue has at least 70%, optionally at least 75%, further optionally at least 80%, still further optionally at least 85%, still further optionally at least 90%, still further optionally at least 95%, still further optionally at least 99%, sequence identity to the amino acid sequence:
MRLSPSLIFVPLVTPAFTLLFNSNLTSPPWLND-LAQRRGKLWFGTAADIPGPEQQDTNYMTI LNDTKIFGELTPANYMKFEYTEPSPNVF-NYSGGDTILAIAENHGKRVRCHN-LIWVSQLPDWV VNGSWTAASLTAVMKTHITN-LITHWGGRCYSWDVVNEALAANGSW ASSIWYDTIGPEYFFL AYRFAQEAVEKTGQDIK-LYYNDYGIEAPGPKTTAAYNLVKELQAR-GIRIDGVGLESHFEVGA TPSKDAQVEAKQGFLD-LGVDVVVTELDVRFPEGPFYTAAGEK QQAQDYYDTVASCVEVGP RCVGITVWDFD-DAYSWVPSSFPGQGAADLYNGTLQRKPAYYA-VAEALQGVSCSVC,
or a fragment thereof.

Optionally, the isolated polypeptide analogue has at least 70%, optionally at least 75%, further optionally at least 80%, still further optionally at least 85%, still further optionally at least least 90%, still further optionally at least 95%, still further optionally at least 99%, sequence identity to the amino acid sequence defined in SEQ ID NO:1, or a fragment thereof.

Optionally, the isolated polynucleotide variant has at least 70% sequence identity to the nucleic acid sequence:
ATGCGTCTCTCTCCGTCTTTAATATTCGTACCGCTGGTCACACCAGCCTTTACATTGCTA TTCAACTCGAACCTCACATCTCCTCCATGGCTCAATGATCTCGCACAGAGGCGTGGCAA GCTGTGGTTTGGCACGGCAGCTGACATCCCCGGTCCAGAGCAGCAGGATACGAACTA CATGACCATCCTGAATGATACGAAGATATTTGGGGAATTGA CGCCTGCGAATTATATGA AGTTCGAATACACTGAACCATCGCCCAATGTCTTCAACTACTCTGGCGGCGACACCATC CTGGCCATCGCCGAAAACCACGGCAA GCGCGTTCGCTGCCAC AACCTCATCTGGGTCAGCCAGCTGCCCGACTGGGTGGTGAACGGCAGCTGGACAGCGGCGAGCCTCACAGCG GTGATGAAGACGCACATCACGAACCTGATCACGCACTGGGG AGGGCGGTGCTACTCG TGGGACGTGGTCAACGAGGCGCTGGCGGCGAACGG GTCGTGGGCGTCCAGCATCTG GTACGACACCATCGGGCCCGAGTACTTCTTCCTCG CGTACCGGTTTGCGCAGGAGGC GGTCGAAAAGACCGGCCAGGACATCAAGCTGTACTACAATGACTACGGGATCGAGGCG CCCGGTCCCAAGACGACGGCGGCGTACAACCTGGT CAAGGAGCTGCAGGCGCGAGG CATCCGGATCGATGGCGTGGGGTTGGAGTCGCATTTCGAAGTGGGCGCGACGCCATC CAAGGACGCGCAGGTTGAGGCCAAGCAGGGGTTTTTGGATCTGGGGGTCGATGTTGT CGTCACGGAGCTGGATGTCAGATTCCCGGAGGGGCCGTTCTACACGGCGGCGG GTGA GAAGCAGCAGGCGCAGGACTATTATGATACGGTGGCGAGCTGCGTGGAGGTTGGTCC TCGGTGTGTGGGCATCACGGTGTGGGATTTTGACGATGCGTATTCGTGGGTGCCGTCA TCGTTTCCTGGACAGGGAGCGGCTGATCTGTATAATGGGACGTTGCAGCGGAAGCCG GCGTACTATGCGGTGGCAGAGGCATTGCAGGGGGTGAGTTGTAGTGTGTGCTAA,
or a fragment thereof.

Optionally, the isolated polynucleotide variant has at least 70% sequence identity to the nucleic acid sequence defined in SEQ ID NO:2, or a fragment thereof.

Optionally, the isolated polynucleotide variant has at least 70%, optionally at least 75%, further optionally at least 80%, still further optionally at least 85%, still further optionally at least 90%, still further optionally at least 95%, still further optionally at least 99%, sequence identity to the nucleic acid sequence:
ATGCGTCTCTCTCCGTCTTTAATATTCGTACCGCTGGTCACACCAGCCTTTACATTGCTA TTCAACTCGAACCTCACATCTCCTCCATGGCTCAATGATCTCGCACAGA GGCGTGGCAA GCTGTGGTTTGGCACGGCAGCTGACATCCCCGGTCCAGAGCAGCAGGATACGAACTA CATGACCATCCTGAATGATACGAAGATATTTGGGGAATTGACGCCT GCGAATTATATGA AGTTCGAATACACTGAACCATCGCCCAATGTCTTCAACTACTCTGGCGGCGACACCATC CTGGCCATCGCCGAAAACCACGGCAAGCGCGTT CGCTGCCACAACCTCATCTGGGTCA GCCAGCTGCCCGACTGGGTGGTGAACGGCAGCTGGACAGCGGCGAGCCTCACAGCG GTGATGAAGACGCACATCACGAACCTGATCACGCACTGGGGAG GCGGTGCTACTCG TGGGACGTGGTCAACGAGGCGCTGGCGGCGAACGGG TCGTGGGCGTCCAGCATCTG GTACGACACCATCGGGCCCGAGTACTTCTTCCT CGCGTACCGGTTTGCGCAGGAGGC GGTCGAAAAGACCGGCCAGGACATCAAGCTGTACTACAATGACTACGGGATCGAGGCG CCCGGTCCCAAGACGACGGCGGCGTACAACCTGGTC AAGGAGCTGCAGGCGCGAGG CATCCGGATCGATGGCGTGGGGTTGGAGTCGCATTTCGAAGTGGGCGCGACGCCATC CAAGGACGCGCAGGTTGAGGCCAAGCAGGGGTTTTTGGATCTGGGGGTCGATGTTGT CGTCACGGAGCTGGATGTCAGATTCCCGGAGGGGCCGTTCTACACGGCGGCGGGTGA GAAGCAGCAGGCGCAGGACTATTATGATACGGTGGCGAGCTGCGTGGAGGTTGGTCC TCGGTGTGTGGGCATCACGGTGTGGGATTTTGACGATGCGTATTCGTGGGTGCCGTCA TCGTTTCCTGGACAGGGAGCGGCTGATCTGTATAATGGGACGTTGCAGCGGAAGCCG GCGTACTATGCGGTGGCAGAGGCATTGCAGGGGGTGAGTTGTAGTGTGTGCTAA,
or a fragment thereof.

Optionally, the isolated polynucleotide variant has at least 70%, optionally at least 75%, further optionally at least 80%, still further optionally at least 85%, still further optionally at least 90%, still further optionally at least 95%, still further optionally at least 99%, sequence identity to the nucleic acid sequence defined in SEQ ID NO:2, or a fragment thereof.

Optionally, the isolated polynucleotide variant has at least 70% sequence identity to the nucleic acid sequence:
ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC
CCT TCC AAG GAT GCT CAG GTT GAA GCT AAA
CAA GGT TTT CTT GAC CTG GGA GTA GAC GTT
GTC GTT ACG GAG TTG GAT GTC CGT TTC CCC
GAG GGC CCT TTT TAC ACC GCA GCT GGA
GAG AAG CAA CAG GCC CAA GAC TAT TAC
GAC ACA GTT GCA AGT TGC GTA GAA GTC GGC
CCC AGG TGC GTG GGC ATT ACT GTC TGG GAC
TTC GAC GAC GCT TAC TCT TGG GTC CCT TCC
TCC TTT CCC GGC CAA GGT GCC GCA GAC CTA
TAC AAT GGT ACT TTA CAG AGG AAG CCT GCT
TAC TAT GCT GTG GCA GAG GCA CTA CAA GGC
GTG TCA TGC AGT GTC TGC TAA, or a fragment thereof.

Optionally, the isolated polynucleotide variant has at least 70% sequence identity to the nucleic acid sequence defined in SEQ ID NO:3, or a fragment thereof.

Optionally, the isolated polynucleotide variant has at least 70%, optionally at least 75%, further optionally at least 80%, still further optionally at least 85%, still further optionally at least 90%, still further optionally at least 95%, still further optionally at least 99%, sequence identity to the nucleic acid sequence:

ATG AGG CTG TCA CCA TCC CTA ATA TTC GTA CCT CTT GTG ACA CCC GCT TTC ACC TTA CTG TTC AAT TCC AAC CTA ACG TCC CCC CCT TGG CTT AAT GAT CTG GCA CAG AGG AGG GGT AAG TTA TGG TTT GGT ACC GCC GCA GAT ATT CCC GGT CCT GAG CAA CAA GAC ACA AAC TAT ATG ACG ATA CTT AAT GAT ACA AAG ATT TTC GGA GAA CTA ACT CCA GCC AAC TAC ATG AAA TTT GAG TAC ACG GAG CCC AGT CCC AAT GTC TTC AAT TAC AGT GGC GGT GAT ACT ATT CTG GCA ATT GCA GAA AAT CAT GGT AAA AGG GTT AGG TGT CAT AAT CTT ATT TGG GTT TCA CAA CTT CCC GAT TGG GTT GTG AAC GGT TCT TGG ACT GCC GCT TCC CTA ACT GCT GTA ATG AAG ACA CAT ATT ACG AAT TTA ATC ACA CAT TGG GGA GGT CGT TGT TAC AGT TGG GAT GTC GTT AAC GAA GCT CTG GCA GCC AAC GGT TCA TGG GCT AGT TCA ATC TGG TAC GAC ACC ATA GGA CCA GAG TAT TTC TTC CTA GCA TAC AGA TTC GCT CAG GAG GCT GTT GAG AAA ACC GGC CAA GAT ATC AAA TTG TAC TAT AAC GAC TAT GGC ATT GAA GCT CCT GGT CCC AAG ACA ACT GCA GCC TAT AAT CTG GTC AAG GAA CTT CAA GCA AGA GGA ATC CGT ATC GAC GGC GTC GGT TTG GAG TCT CAT TTT GAG GTG GGA GCA ACC CCT TCC AAG GAT GCT CAG GTT GAA GCT AAA CAA GGT TTT CTT GAC CTG GGA GTA GAC GTT GTC GTT ACG GAG TTG GAT GTC CGT TTC CCC GAG GGC CCT TTT TAC ACC GCA GCT GGA GAG AAG CAA CAG GCC CAA GAC TAT TAC GAC ACA GTT GCA AGT TGC GTA GAA GTC GGC CCC AGG TGC GTG GGC ATT ACT GTC TGG GAC TTC GAC GAC GCT TAC TCT TGG GTC CCT TCC TCC TTT CCC GGC CAA GGT GCC GCA GAC CTA TAC AAT GGT ACT TTA CAG AGG AAG CCT GCT TAC TAT GCT GTG GCA GAG GCA CTA CAA GGC GTG TCA TGC AGT GTC TGC TAA, or a fragment thereof.

Optionally, the isolated polynucleotide variant has at least 70%, optionally at least 75%, further optionally at least 80%, still further optionally at least 85%, still further optionally at least 90%, still further optionally at least 95%, still further optionally at least 99%, sequence identity to the nucleic acid sequence defined in SEQ ID NO:3, or a fragment thereof.

Optionally, the promoter is an inducible promoter. Alternatively, the promoter is a constitutive promoter.

Optionally, the promoter is selected from the AOX1 promoter, the AOX2 promoter, the FLD1 promoter, the DAS promoter, the PEX8 (PER3) promoter, the YPT1 promoter, the GAP promoter, the TEF1 promoter, the PGK1 promoter, and the ICL1 promoter.

Alternatively, the promoter is selected from the tet promoter, the T7 promoter, the T3 promoter, the araBAD promoter, the T7-lac promoter, the tac promoter, the PL promoter, the trc promoter, the T5/lac promoter, the trc/lac promoter, the PLtetO-1 promoter, the PLlacO-1 promoter, the polyhedrin promoter, and the Plac/ara-1 promoter.

Alternatively, the promoter is selected from the GlaPr glucoamylase promoter.

Optionally, the host cell is a recombinant host cell. Further optionally, the host cell is a fungal host cell. Still further optionally, the host cell is a recombinant fungal host cell.

Optionally, the host cell is a Trichocomaceae family cell. Further optionally, the host cell is a *Rasamsonia* cell. Still further optionally, the host cell is selected from at least one of a *Rasamsonia aegroticola* cell, a *Rasamsonia argillacea* cell, a *Rasamsonia brevistipitata* cell, a *Rasamsonia byssochlamydoides* cell, a *Rasamsonia columbiensis* cell, a *Rasamsonia composticola* cell, a *Rasamsonia cylindrospora* cell, a *Rasamsonia eburnean* cell, a *Rasamsonia emersonii* cell, a *Rasamsonia piperina* cell, and a *Rasamsonia pulvericola* cell. Still further optionally, the host cell is a *R. emersonii* cell.

Further optionally, the host cell is an *Aspergillus* cell. Still further optionally, the host cell is selected from at least one of an *Aspergillius niger* cell and an *Aspergillius awamori* cell.

Optionally, the host cell is an *Incertae sedis* family cell.

Optionally, the host cell is a *Scytalidium* cell. Further optionally, the host cell is selected from at least one of an *S. thermophilum* cell, an *S. album* cell, an *S. aurantiacum* cell, an *S. circinatum* cell, an *S. dimidiatum* cell, an *S. flavobrunneum* cell, an *S. hyalinum* cell, an *S. indonesiacum* cell, an *S. infestans* cell, an *S. japonicum* cell, an *S. multiseptatum* cell, an *S. muscorum* cell, an *S. terminale* cell, an *S. uredinicola* cell, and an *S. vaccinia* cell. Still further optionally, the host cell is an *S. thermophilum* cell, Optionally, the host cell is a Chaetomiaceae family cell.

Optionally, the host cell is a *Myceliophthora* cell. Further optionally, the host cell is selected from at least one of a *Myceliophthora fergusii* cell, a *Myceliophthora thermophilacell*, a *Myceliophthora lutea* cell, a *Myceliophthora vellerea* cell, and a *Myceliophthora hinnulea* cell. Still further optionally, the host cell is a *Myceliophthora fergusii* cell, Optionally, the host cell is a recombinant host cell. Further optionally, the host cell is a bacterial host cell. Still further optionally, the host cell is a recombinant bacterial host cell.

Optionally, the host cell is an Enterobacteriaceae family cell. Further optionally, the host cell is an *Escherichia* cell. Still further optionally, the host cell is an *E. coli* cell.

Optionally, the host cell is a recombinant host cell. Further optionally, the host cell is a yeast host cell. Still further optionally, the host cell is a recombinant yeast host cell.

Optionally, the host cell is a Saccharomycetaceae family cell. Further optionally, the host cell is a *Pichia* cell. Still further optionally, the host cell is a *P. Pastoris* cell.

The invention provides a host cell, comprising a polynucleotide of the invention operably linked to one or more control sequences that direct the production of a polypeptide of the invention, e.g. in the form of the nucleotide construct or the vector as described herein (supra). The host cell is preferably recombinant. The construct or vector comprising the polynucleotide of the invention may be introduced into a host cell so that the construct or vector is maintained as a chromosomal integrant or as a self-replicating extra-chromosomal vector as described supra. The term "host cell" encompasses any progeny of a parent cell that is not identical to the parent cell due to mutations that occur during replication. The choice of a host cell will to a great extent depend upon the gene encoding the polypeptide and its source.

The host cell may be any cell useful in the recombinant production of a polypeptide of the present invention, particularly eukaryotes.

Strains of suitable host cell microorganisms are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), Agricultural Research Service Patent Culture Collection, Northern Regional Research Center (NRRL) and All-Russian Collection of Microorganisms of Russian Academy of Sciences, (abbreviation in Russian—VKM, abbreviation in English—RCM), Moscow, Russia.

In a particular embodiment, the host cell may is eukaryote, such as a mammalian, insect, plant, or fungal cell. The host cell is preferably a fungal cell. "Fungi" as used herein include the phyla Ascomycota, Basidiomycota, Chytridiomycota, and Zygomycota as well as the Oomycota and all mitosporic fungi as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacterial. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth by hyphal elongation and carbon catabolism is obligately aerobic. In contrast, vegetative growth by yeasts such as *Saccharomyces cerevisiae* by budding of a unicellular thallus and carbon catabolism may be fermentative. The filamentous fungal host cell may be an *Acremonium, Aspergillus, Aureobasidium, Bjerkandera, Ceriporiopsis, Chrysosporium, Coprinus, Corio/us, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Corio/us hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Useful fungal strains in the context of the present invention may be *Aspergillus niger* (CBS 513.88 and/or CBS 124.903), *Aspergillus oryzae* (ATCC 20423, IFO 4177, ATCC 1011, CBS205.89, ATCC 9576, ATCC14488-14491, ATCC 11601 and/or ATCC 12892), *P. chrysogenum* (CBS 455.95, ATCC 28089 and/or P2), *Penicillium citrinum* (ATCC 38065), *Thielavia terrestris* (NRRL8126), *Talaromyces emersonii* (CBS 124.902), *Acremonium chrysogenum* (ATCC 36225 and/or ATCC 48272), *Trichoderma reesei* (ATCC 26921, ATCC 56765 and/or ATCC 26921), *Aspergillus sojae* (ATCC 11906), *Myceliophthora thermophila* (C1, Garg 27K and/or VKM-F 3500 D), *Chrysosporium lucknowense* (C1, Garg 27K, VKM-F 3500 D and/or ATCC 44006) and derivatives thereof.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacterial. 153: 163; and Hinnen et al., 1978, Proc. Natl. Acad. Sci. USA 75:1920.

The host cell of the invention may also be altered by deleting, knocking-out or disrupting one or more genes in full or in part.

The host cell of the invention may be formulated into a liquid or dry preparation. Dry formulations include lyophilizing, flash freezing or encapsulating the host cell.

According to a seventh aspect of the present invention, there is provided a method of degrading lignocellulose biomass, the method comprising the steps of:
 (a) providing a lignocellulose biomass; and
 (b) contacting the lignocellulose biomass with an isolated polypeptide comprising the amino acid sequence:

MRLSPSLIFVPLVTPAFTLLFNSNLTSPPWLND-
LAQRRGKLWFGTAADIPG PEQQDTNYM-
TILNDTKIFGELTPANYMKFEYTEPSPNVF-
NYSGGDTILAIAE
NHGKRVRCHNLIWVSQLPDWVVNG-
SWTAASLTAVMKTHITNLITHWGGR
CYSWDVVNEALAANGSWASSIWYDTIGPEYF-
FLAYRFAQEAVEKTGQDIK LYYNDY-
GIEAPGPKTTAAYNLVKELQARGIRIDGV-
GLESHFEVGATPSKDA
QVEAKQGFLD-
LGVDVVVTELDVRFPEGPFYTAAGE
KQQAQDYYDTVASC VEVGPRCVGITVWDFD-
DAYSWVPSSFPGQGAADLYNGTLQRK-
PAYYAVA EALQGVSCSVC, or a fragment or analogue thereof.

Optionally, the contacting step (b) of the method of degrading lignocellulose biomass is conducted at a pH of greater than 2.5. Optionally or additionally, the contacting step (b) of the method of degrading lignocellulose biomass is conducted at a pH of less than 6.0.

Optionally, the contacting step (b) of the method of degrading lignocellulose biomass is conducted at a pH of 3.0-6.0. Further optionally, the contacting step (b) of the method of degrading lignocellulose biomass is conducted at a pH of 3.5-6.0. Still further optionally, the contacting step (b) of the method of degrading lignocellulose biomass is conducted at a pH of 3.5-5.5. Still further optionally, the contacting step (b) of the method of degrading lignocellulose biomass is conducted at a pH of 4.0-5.5. Still further optionally, the contacting step (b) of the method of degrading lignocellulose biomass is conducted at a pH of 4.0-5.0. Still further optionally, the contacting step (b) of the method of degrading lignocellulose biomass is conducted at a pH of 4.5-5.0. Still further optionally, the contacting step (b) of the method of degrading lignocellulose biomass is conducted at a pH of 4.0-4.5.

Optionally or additionally, the contacting step (b) of the method of degrading lignocellulose biomass is conducted at a temperature of greater than 45° C. Optionally or additionally, the contacting step (b) of the method of degrading lignocellulose biomass is conducted at a temperature of less than 90° C.

Optionally or additionally, the contacting step (b) of the method of degrading lignocellulose biomass is conducted at a temperature of 45-90° C. Further optionally or additionally, the contacting step (b) of the method of degrading lignocellulose biomass is conducted at a temperature of 50-85° C. Still further optionally or additionally, the contacting step (b) of the method of degrading lignocellulose biomass is conducted at a temperature of 55-80° C. Still further optionally or additionally, the contacting step (b) of the method of degrading lignocellulose biomass is conducted at a temperature of 60-75° C. Still further optionally or additionally, the contacting step (b) of the method of degrading lignocellulose biomass is conducted at a temperature of 65-75° C. Still further optionally, the contacting step (b) of the method of degrading lignocellulose biomass is conducted at a temperature of 70-75° C.

BRIEF DESCRIPTION OF THE DRAWINGS

Embodiments of the present invention will now be described with reference to the accompanying drawings, in which.

EXAMPLES

Embodiments of the present invention will now be described with reference to the following non-limiting examples:

Example 1

Amplification of the Isolated Polypeptide (Xyn1)

PCR reactions were carried out using insert-containing vector as a template (ordered from Eurofins) and Herculase II Fusion polymerase from Agilent Technologies Ireland. The primers used in the amplification of xyn1 are listed in Table 1 and the PCR cycle parameters are listed in Table 2. The primers were designed to omit the signal sequence of each sequence.

TABLE 1

PCR primers designed to amplify xyn1 gene from a gene library. All genes were sub-cloned into pICZα vectors.

| Enzyme | Vector | Signal Sequence | Restriction enzyme | Forward primer |
|---|---|---|---|---|
| Xyn 1 | pICZα A | 1-18 | EcoR1 | gggggaattcTT GCTATTCAACTC GAACC |
|  |  |  | Xba1 | ggggtctagagt GCACACACTACA ACTCACC |

TABLE 2

PCR conditions for amplifying DNA from PJET vectors.

| Temperature (° C.) | Time | Number of cycles |
|---|---|---|
| 95 | 2 min | 1 |
| 95 | 20 s |  |
| 58 | 20 s | 35 |
| 72 | 45 s |  |
| 72 | 5 min | 1 |

Figure 1:
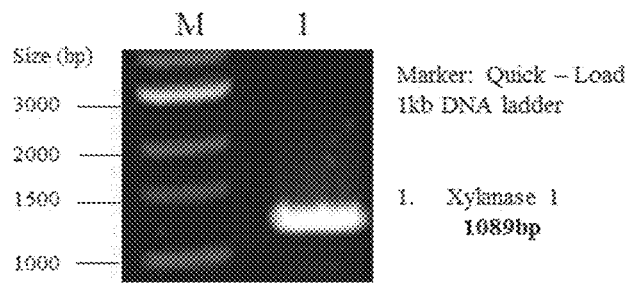
FIG. 1 is an agarose gel illustrating PCR amplification of xyn1 from a gene library.

After the PCR reaction cycles described above were complete, the DNA samples were loaded onto the agarose gel (FIG. 1). The DNA ladder; Quick-Load 1 kb DNA ladder form New England Biolabs, was loaded into lane "M" and was used to track the progression of the samples through the gel. The ladder is fully separated indicating that the electrophoresis has run effectively. Upon comparison to the DNA ladder under UV light, the bright bands of amplified DNA can be seen to occur in the expected region, indicating that the amplification reaction was successful. No unspecific amplification can be seen.

Restriction Enzyme Digestion of DNA

The restriction enzymes EcoRI, and XbaI (Fast Digest from Thermo Scientific) were chosen for the digestion reactions as there are no recognition sites within the target gene. The purified PCR product and purified plasmid were restricted as per manufacturer's instruction at 37° C. for 15 min. Alkaline Phosphatase (AP) (Thermo Scientific) was added to the reaction mixture, as per manufacturer's instructions. AP removes a phosphate group from the 5' end of the pICZα vector, thus preventing self-ligation of the vector during the ligation step.

Ligation of Digested DNA

Ligation of the restricted gene and plasmid was carried out using T4 DNA ligase as per manufacturer's instructions. All ligation reactions were carried out at 22° C. for 20 min or at room temperature overnight. The T4 DNA ligase was inactivated by heating to 65° C. for 10 min.

Preparation of Electro-Competent E. coli Cells

E. coli strains were rendered competent as described in Sambrook and Russell (2001) with minor modifications. Briefly, log-phase cells were prepared from 16 h cultures that were diluted 1/100 and incubated at 37° C. for 3-4 h to an optical density measurement of about 0.6 at 600 nm. Cells were harvested by centrifugation for 10 min at 4,000×g at 4° C. The cells were re-suspended in 50 mL sterile ice-cold 10% glycerol solution, centrifuged as before, and re-suspended in 25 mL of the 10% glycerol solution; centrifuged as before, and re-suspended in 10 mL of glycerol solution; centrifuged as before, and re-suspended in 10% glycerol solution to a final volume of 1 mL. The cells were aliquoted (50 µL) into microfuge tubes, snap frozen with liquid nitrogen, and stored at –80° C.

Preparation of Electro-Competent P. pastoris Cells

P. pastoris X-33 cells were made electro-competent as per methods developed in-house. Briefly, a swab of P. pastoris X-33 glycerol stock was used to inoculate 100 mL of Yeast Extract-Peptone-Dextrose (YPD) broth in a 500 mL baffled flask. The culture was grown at 30° C. with gentle agitation of 180 rpm, until the culture reached an OD600=4-6 (approximately 16 h). The cells were harvested at 1,500×g for 5 min at 4° C. and re-suspended in sterile "Solution A", containing 10 mL YPD, 250 µL 1M DTT and 200 µL HEPES in a 50 mL conical centrifuge tube. The conical centrifuge tube was incubated at a 45° angle, 30° C. and 180 rpm for 15 min. 40 mL of ice-cold sterile MQ H2O was added to the conical centrifuge tube. The cells were centrifuged as before, the supernatant was discarded, and the cells were and gently re-suspended in 25 mL of ice-cold 1 mM HEPES. The cells were centrifuged as before, the supernatant was discarded, and the cells were and gently re-suspended in 5 mL of ice-cold 1 M sorbitol. The electro-competent cells were kept on ice and used the same day.

Transformation of DNA into Electro-Competent E. coli

Plasmids were introduced into competent E. coli cells by known electroporation methods (Dower et al., 1988) with minor changes. Competent cells were removed from the –80° C. freezer and allowed to thaw on ice. Plasmid DNA/ligation mixture containing 10-100 ng of DNA was added to 50 µL of competent cells, gently mixed and then transferred to a pre-chilled electroporation cuvette. The cuvette was dried, placed inside the electroporation device and electroporated at: voltage=1.8 kV, capacitance=25 µF, resistance=200Ω. 1 mL of LB (Luria low salt) broth was added immediately to the cells. Cells were grown at 37° C. for 1 h without agitation. Cells were then concentrated appropriately and 100 µL of the culture spread on LB low salt plates containing the appropriate amount of zeocin antibiotic. During every transformation, a positive control of empty vector and a negative control of H2O were also electroporated under the same conditions described herein.

E. coli containing the insert-pICZα plasmids vector were grown overnight at 37° C., 250 rpm in 5 mL of LB low salt broth supplemented with the appropriate amount of zeocin antibiotic. High purity plasmid DNA for the use of transformation into P. pastoris cells was purified using the HiYeild Plasmid Mini Kit. The DNA samples were linearized by incubation with PmeI (Fast Digest from Thermo Scientific) restriction enzyme at 37° C., for 10 min, as per manufacturer's instructions. The PmeI restriction recognition site is included in the pICZα vectors sequence. To concentrate the DNA for transformation, the samples of linearized DNA were pooled and concentrated by ethanol precipitation as per Sambrook and Russel (2001) and re-suspended in 15 µL H2O. The final concentration of DNA should be no less than 0.5 µg per µL.

Transformation of DNA into Electro-Competent P. pastoris

An aliquot of 80 µL of the electro-competent P. pastoris cells was gently mixed with 5-10 µg of linearized clone plasmid DNA and transferred to an ice-cold 0.2 cm electroporation cuvette. The cuvette containing the cells is incubated on ice for 5 min. The cuvette was dried and pulsed in the electroporator under the manufacturer's instructions for Saccharomyces cerevisiae (1750, 2500V, 50 µF). Immediately, 1 mL of ice-cold YPD broth was added to the cuvette. The contents of the cuvette were transferred to a sterile 15 mL tube and incubated at 30° C. without shaking for 1-2 h. The samples were either stored at –80° C. at this point or spread on zeocin-containing YPD plates. When plating transformants, a 100 µL aliquot of electro-porated cells were each spread on separate, labelled YPD plates containing 100, 500 and 1000 µg/mL zeocin. Plates were incubated for up to 3 days at 30° C. until colonies formed. During every transformation, a positive control of empty pICZα vector and a negative control of H2O were also electro-porated under the same conditions described herein.

Screening for Transformations in E. coli

Screening of transformants was achieved using the MyTaq Red mix from Bioline. PCR on colonies was performed with the 5'AOX1 and 3'AOX1 primers and as per the manufacturer's instructions. The PCR-on-colonies reactions were visualised on agarose gel electrophoresis in 1.0% (w/v) agarose gels stained with SybrSafe according to standard procedures by Sambrook and Russell (2001).

Figure 2:
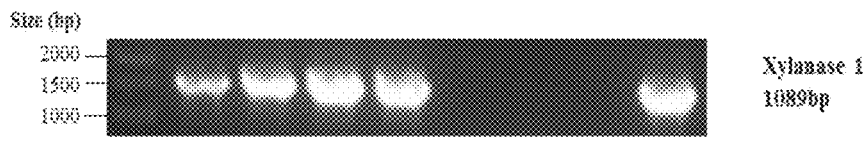
FIG. 2 is an agarose gel illustrating screening for clones from PCR-on-colonies of xyn1 transformants.

Colonies positive for the target-inserts were visualised as bright bands at the appropriate-size region upon comparison of the standard DNA ladder (FIG. 2). Clones which yielded the brightest DNA bands were used the transformation into P. pastoris procedure.

Screening for Transformations in P. pastoris

Positive transformants in P. pastoris are visualised as single P. pastoris colonies on zeocin selective YPD (Yeast Peptone, Dextrose) plates after 2-3 days of incubation at 30° C.

Expression Screening

P. pastoris colonies that formed on the zeocin-selective YPD plates after transformation were used to inoculate 2 mL of Buffered Glycerol-complex Medium (BMGY), respectively. The cultures were incubated for 16 h. After the incubation period, the cells were harvested by centrifuging for 10 min at 3,000×g. The OD600 of the cells had been measured prior to harvesting and the appropriate amounts of each culture required to inoculate the media to an OD600 of 1 were re-suspended in 2 mL Buffered Methanol-complex, Medium (BMMY). The cells were then re-suspended in 2 mL of BMMY media to induce expression, and they were incubated as before. The media was supplemented with 100% methanol every 24 h to a final volume of 1% to maintain expression. At 48 h of incubation the cells were harvested as before, and underwent protein-presence and activity screening. As a negative control, a sample of empty-vector *P. pastoris* cells underwent the same protein expression screening and analysis conditions.

Activity Screening

Figure 3:
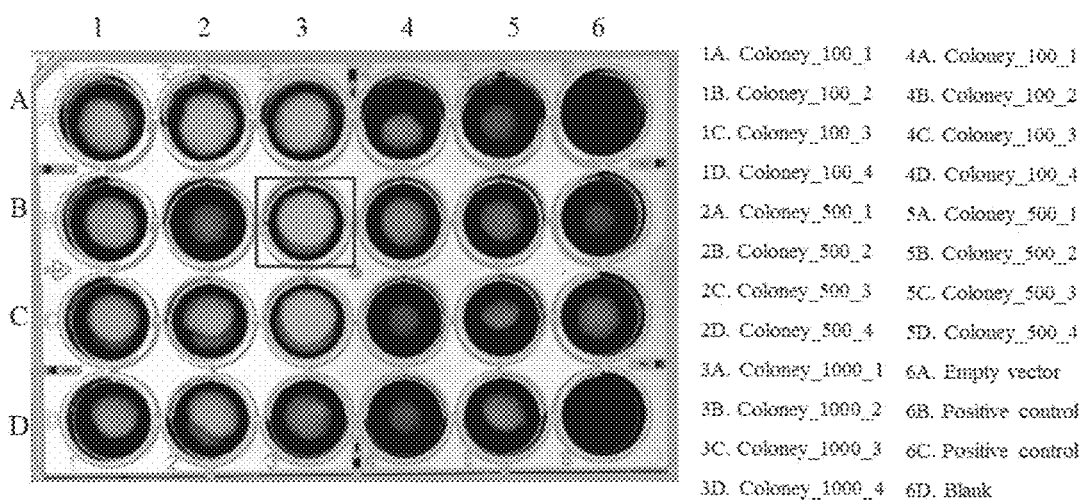
FIG. 3 illustrates Xylanase activity screening of xyn1 colonies.

A solution containing 0.2% Azo-Xylan from Birchwood and agar in 100 mM sodium acetate pH 5 was made up and dispensed into a 24-well plate in 500 µL aliquots. Once the plate had set, a sample of each of the expression samples was placed onto each of the 24 well, respectively. The plate was then incubated at 60° C. for 1 h. A positive control of commercial xylanase from Megazymes Ireland and a negative control of empty vector expression sample were subjected to the same activity screening conditions. Xylanase activity was visualised as a zone of clearance in the 0.2% Azo-xylan agar. The highest xylanase expressing transformant was determined by measuring the largest zone of clearance. Upon comparison of the 0.2% xylan agar plate to the SDS-PAGE gel obtained via the method described herein, the highest expresser was isolated from well B3 (FIG. 3).

Expression, Expression Curve and Expression Timeline

Growth of plasmid-containing *Pichia pastoris* X-33 strains was undertaken in accordance with instructions obtained from the EasySelect *Pichia* Expression Kit from Invitrogen by Life Technologies with some modifications. To obtain an expression curve and timeline, a sample of the highest expressing *P. pastoris* cells was taken from glycerol stock and cultured on YPD agar as described herein. Well-isolated, single colonies were used to inoculate flasks of 25 mL BMGY pre-culture, respectively. These were incubated at 30° C., 250 rpm until they reached an OD600 of approximately 5. The respective amounts required of each sample were then harvested by centrifugation at 1,500×g for 5 min at room temperature and re-suspended to an OD600 of 1, in 100 mL BMMY in baffled flasks. The baffled flasks were covered breathable membrane; either 2 layers of sterile cheesecloth or a breathable bottle-top lid to allow for aeration of the expression cultures. The expression cultures were then incubated at 30° C., 250 rpm. 100% methanol was added to bring the flasks to a final volume of 1% methanol every 24 hours to maintain induction. To obtain an expression curve and timeline, samples of 1 mL were taken from each flask every 24 h up to 216 h of expression.

Figure 4:
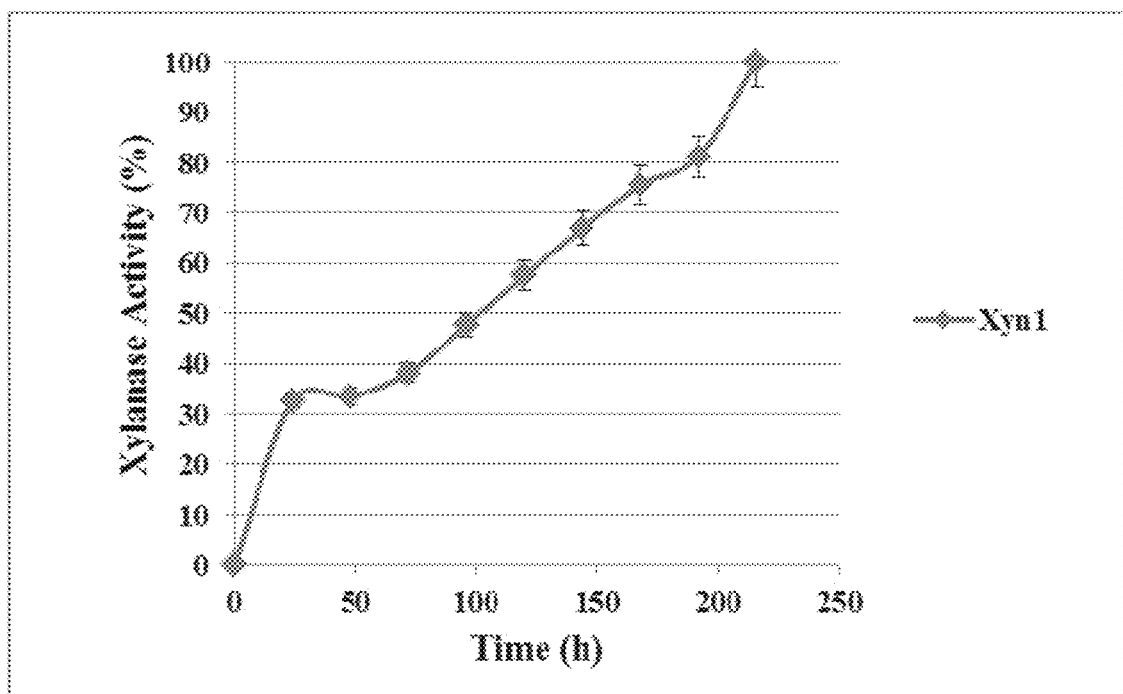
FIG. 4 illustrates an activity analysis of xyn1 expression.

The 1 mL samples were centrifuged at in a table top centrifuge at max speed for 3 min. The supernatant was collected and a sample was loaded on a 10% SDS-PAGE gel and subjected to electrophoresis to visualise the increase in recombinant protein present per mL of expression media over the time points. Activity assays were carried out on the samples to measure the increase in activity per ml of expression media (FIG. 4).

Expression samples which were used in purification and/or characterisation studies were harvested at 48 h. Proteases are known to be increasingly present in the secretome of the *P. pastoris* cells after this time, particularly where expression has been induced by methanol. During expression, degradation of the recombinant enzymes was initially visualised during zymogram activity analysis, thus the expression time for all samples was reduced to 48 h.

Identification of the Xyn1 Polypeptide

Polyacrylamide gel electrophoresis under both denaturing (SDS-PAGE) and non-denaturing conditions was employed as per standard methods. For xylanase zymograms, both native and denaturing PAGE techniques were employed. Ten percent native/SDS PAGE gels (Laemmli, 1970) were created containing 0.2% Azo-Xylan from Beechwood. The loading buffers contained no DTT.

Figure 5:
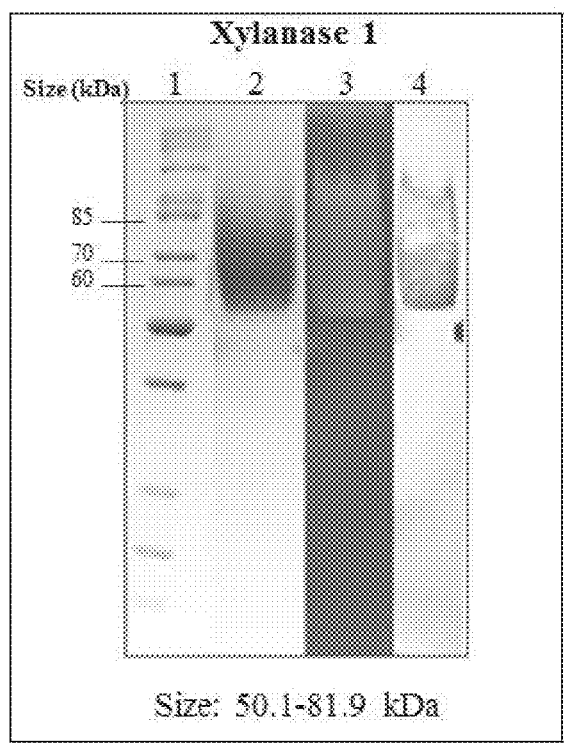
FIG. 5 Illustrates identification of xyn1 protein through SDS-PAGE, zymogrphy and western blot analysis.
Figure 11:
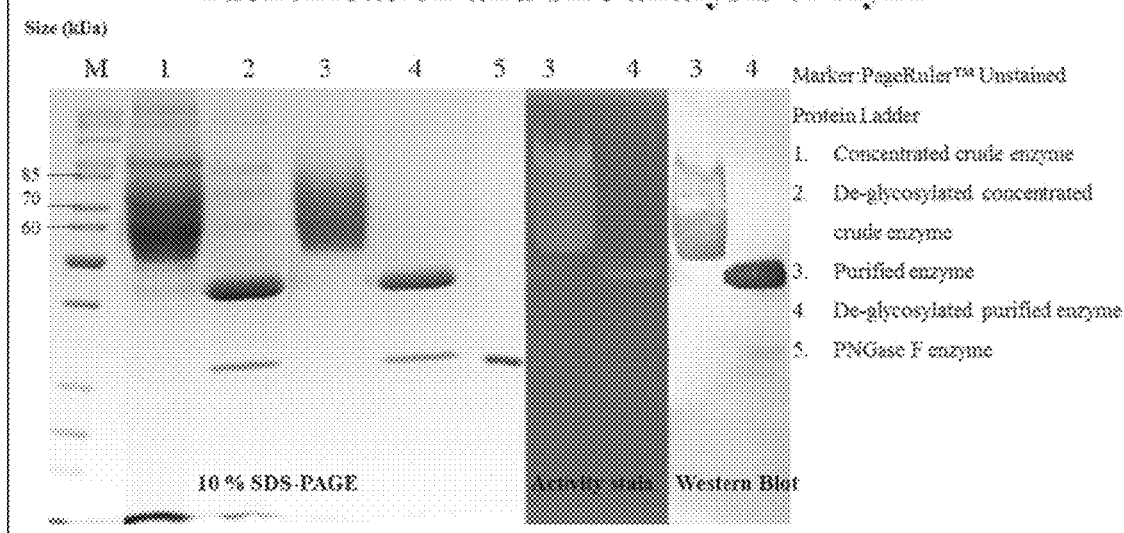
FIG. 11 illustrates size analysis of xyn1 through SDS-PAGE, zymography and western blot.

For the native zymogram, the gel and buffers contained and no SDS. Once run, the gels were incubated in 50 mM citrate buffer pH 4.5 for 20 min and 4 h for native and denatured gels, respectively, to allow activity of the xylanase enzymes against the embedded substrate. The denatured gel was incubated in dH2O at 30° C. for 30 min prior to incubation at pH 4.5 to remove SDS from the gel and encourage retention of xylanase activity. The gels were then stained red with congo red and de-stained with NaCl. Xylanase activity can be visualised as clearance zones on the red gels (FIGS. 5 and 11). Western blot was employed as per standard methods.

De-Glycosylation Reaction with PNGase F

De-glycosylation procedure was carried out on both the native and denatured recombinant protein using PNGase F enzyme from New England Biolabs, as per manufacturer's instructions. The denatured de-glycosylated protein was loaded onto a 10% SDS gel and subjected to electrophoresis. The samples were also subjected to zymogram analysis and Western Blot analysis as described herein. The de-glycosylated native protein was subjected to electrophoresis via native PAGE as described herein. In all cases, a sample of glycosylated recombinant protein and a negative control of H2O and PNGase F solution were run on the same gels for identification of the PNGase F on the gel.

Purification of Recombinant Proteins

Hispur Colbalt and His Pur Ni-NTA resin was obtained from ThermoFisher Scientific. Purification columns and equipment, i.e. filters, lids, were obtained from thermoscientific. Slide-A-lizer dialysis cassettes were obtained from Thermo Fisher Scientific.

In the case of Colbolt resin: an initial sample of expression culture of 100 mL contained approximately 95 mL of crude supernatant after harvesting at 48 h of induction. After harvesting at 3000×g for 10 min at 4° C., the crude expression samples were concentrated using a 50 mL Amicon Stirred Ultrafiltration Cell (Millipore) as per manufacturer's instructions. A typical concentration of approximately 20 mL was achieved by using a Millipore 10 kDa cut off ultrafiltration membrane (Sigma) with 70 psi of N2 being applied to the unit. The concentrated supernatant containing the recombinant enzyme is approximately pH 4.0. The crude supernatant sample was equilibrated by diafiltrating with purification equilibrium buffer (50 mM sodium phosphate, 300 mM sodium chloride, pH 7.4). The buffer was added to the concentrated supernatant to a volume of 50 mL and re-concentrating as before, until the amount of concentrated sample is 15-20 mL. This step was repeated until the pH of the enzyme sample was above/equal to pH 6.5. Ultrafiltration/diafiltration runs were carried out at room temperature. The diafiltrated sample and flow through was assayed for activity to ensure no large loss of enzyme occurred. Millipore membranes were stored in 10% (v/v) ethanol at 4° C. With both the Colbalt and Ni-NTA resin protocols, the equilibrated concentrated supernatant containing the recombinant enzyme was purified that day to avoid proteolytic degradation of the enzyme.

Immobilized Metal Chelating Chromatography

The chromatographic technique that was carried out using HisPur Cobalt resin is as follows: concentrated protein (15-20 mL) was loaded into a 1×6.0 cm econo-column (Bio-Rad) packed with HisPur Cobalt with a bed volume of 3.0 mL. The column had been pre-equilibrated with equilibration buffer (50 mM sodium phosphate, 300 mM sodium chloride, pH 7.4). The purifications were carried out at 4° C. using the Biologic LP purification system. During the wash step, equilibrium buffer was run through the column at a flow rate of 1 mL/min. The elution buffer (50 mM sodium phosphate, 300 mM sodium chloride, 150 mM imidazole; pH 7.4) was then run through the column at the same flow rate. Fractions of 3.0 mL were collected, assayed for the appropriate activity, and protein concentration by absorbance at 280 nm was recorded continuously throughout the run by Biologic LP Dataview Software. Recombinant protein containing fractions were pooled, assayed for total activity and total protein content by Bradford assay.

The chromatographic technique that was carried out using Ni-NTA Cobalt resin is as follows: equilibrated protein (150 mL) was loaded into a 1×6.0 cm column (Thermo Fisher) packed with Ni-NTA resin with a bed volume of 1.0 mL. The column had been pre-equilibrated with equilibration buffer (20 mM sodium phosphate, 300 mM sodium chloride, 20 mM Imidizole pH 7.4). The purifications were carried out at room temperature using gravity flow. Washes were carried out as 2×2 mL washes containing increasing concentrations of imidazole (20 mM, 40 mM, 75 mM, 100 mM, 150 mM and 250 mM). Fractions of 2.0 mL were collected, assayed for the appropriate activity, and protein concentration by absorbance at 280 nm was recorded using the nanodrop equipment. Recombinant protein containing fractions were pooled, assayed for total activity and total protein content by Bradford assay.

Diafiltration of Purified Enzymes

In the case that Colbalt resin was used during purification, the enzyme was diafiltrated with diafiltration buffer (100 mM citrate buffer pH 4.5) using a 50 mL Amicon Stirred Ultrafiltration Cell (Millipore) and a Millipore 10 kDa cut off ultrafiltration membrane (Sigma) with 70 psi of N2 being applied to the unit, as per manufacturer's instruction. Ultrafiltration/diafiltration runs were carried out at room temperature. The diafiltrated sample and flow through was assayed for activity to ensure no large loss of enzyme occurred. Sterilised glycerol was added to the dialysed, purified protein sample to a final concentration of 20%. The sample was stored in 1 mL aliquots at −20° C. thereafter. In the case that Ni-NTA resin was used during purification, the enzyme was dialysed with dialysis buffer (50 mM citrate buffer pH 4.5/5) using the 3 mL slide-A-lizer kit from Thermo Fisher, as per manufacturer's manual. Dialysis runs were carried out at 4° C. overnight. Sterilised glycerol was added to the dialysed, purified protein sample to a final concentration of 20%. The sample was stored in 1 mL aliquots at −20° C. thereafter.

Xylanase Assay

The assay used for estimation of endo-1,4,β-xylanase activity was based on methods by Miller, 1959 with some modifications. Both cuvette and microtiter methods were employed. The cuvette assay system contained 250 µL of 1% xylan from Beechwood, and 250 µL of suitably diluted enzyme in 100 mM citric acid, at the appropriate pH. The reaction was allowed to proceed for 15 min at the desired assay temperature, and was stopped by the addition of 750 µL of 3,5-dinitrosalicylic acid (DNS). Both substrate solution and enzyme were equilibrated to assay temperature prior to initiation of the reaction. An assay blank contained enzyme and substrate solution, which were incubated separately for the duration of the reaction period and mixed only after addition of stopping solution to the substrate.

The microtiter assay system contained 100 µL of 1% xylan from Beechwood in 150 mM citric acid, at the appropriate pH, and 100 µL of suitably diluted enzyme in H2O. The reaction was allowed to proceed for 15 min at the desired assay temperature and was stopped by the addition of 50 µL reaction sample to 100 µL 3,5-dinitrosalicylic acid (DNS). Both substrate solution and enzyme were equilibrated to assay temperature prior to initiation of the reaction. An assay blank contained enzyme and substrate solution, which were incubated separately for the duration of the reaction period and mixed in the required amounts directly with the stopping solution. All samples are heated at 95° C. for 5 min and immediately cooled on ice for 10 min. The absorbance of the assay solution was measured after cooling to room temperature at 540 nm with a UV-visible spectrophotometer, blanked with dH2O.

As the reaction of endo-1,4,β-xylanase and xylan leads to the release of reducing sugars, one of which is xylose, two sets of standard curves were constructed to quantify the amount released during the assay; one of 500 µL and one of 50 µL of various xylose concentrations. Xylose standard solutions were prepared in triplicate by diluting a stock solution of 1% xylose in either 50 or 75 mM citrate buffer. Standard solutions ranged from 0-8 µmol xylose/mL. Construction of the standard curve was carried out by mixing 500 µL xylose and 750 µL DNS or 50 µL xylose and 100 µL DNS (stopping) solution, respectively, heating and cooling as described in this section previously, and subsequently determining absorbency values at 540 nm.

From the standard curve, the amount of xylose released during the assay could be determined and this was used to calculate endo-1,4,β-xylanase activity. One unit of endo-1,4,β-xylanase activity was defined as the amount of enzyme capable of releasing 1 µmol of xylose/min/mL under the defined assay conditions. Using the method above and the Bradford assay, the specific activity of the xylanases could be calculated. Specific activity of the endo-1,4,β-xylanase activity was defined as the amount of enzyme capable of releasing 1 µmol of xylose/min/mg under the defined assay conditions.

Example 2

Determination of pH Versus Activity Profiles

Figure 6:
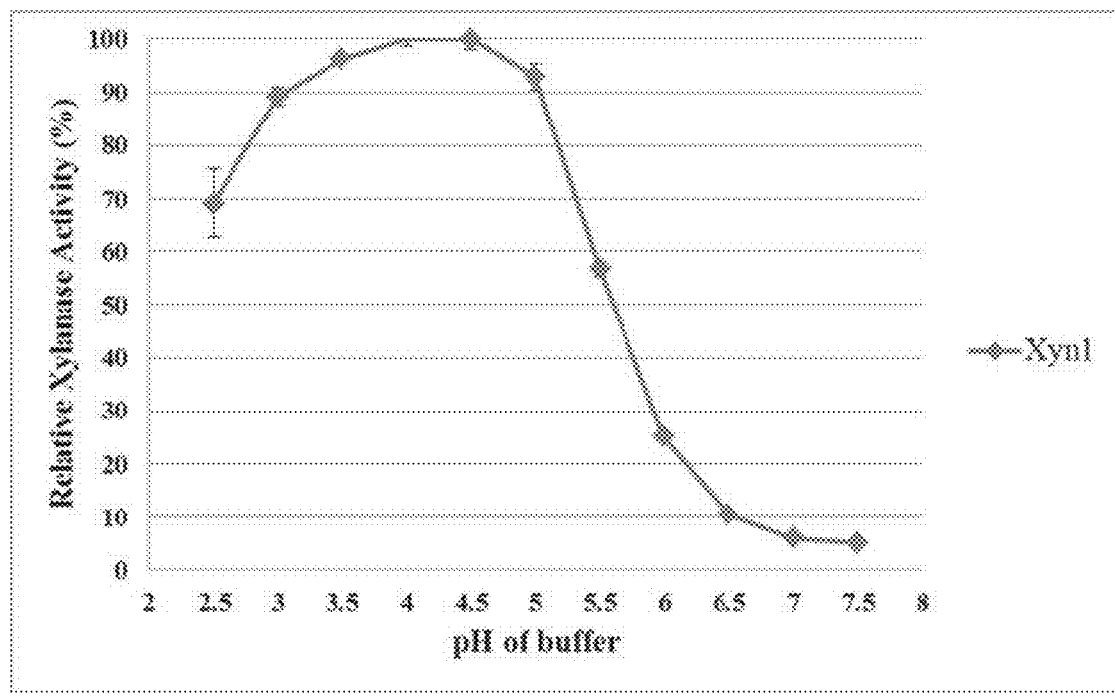
FIG. 6 illustrates pH versus activity profiles of xyn1.

Activity versus pH profiles were obtained for the purified enzymes according to the methods of Kamble et al., 2012; Liao et al., 2015; and Miller, 1959; with some modifications. Each enzyme was assayed for activity in triplicate by the standard assay procedure as described herein. The pH values tested were pH 2.5, 3.0, 3.5, 4.0, 4.5, 5.0, 5.5 and 6.0 in 100 mM citrate buffer. The results were plotted as either percentage relative activity. The relative xylanase activity at the various pH values was determined as a percentage of the pH where optimum activity was observed. Percent relative activity verses pH was plotted to yield the pH profile for the enzymes (FIG. 6).

Example 3

Determination of Temperature Versus Activity Profiles

Figure 7:
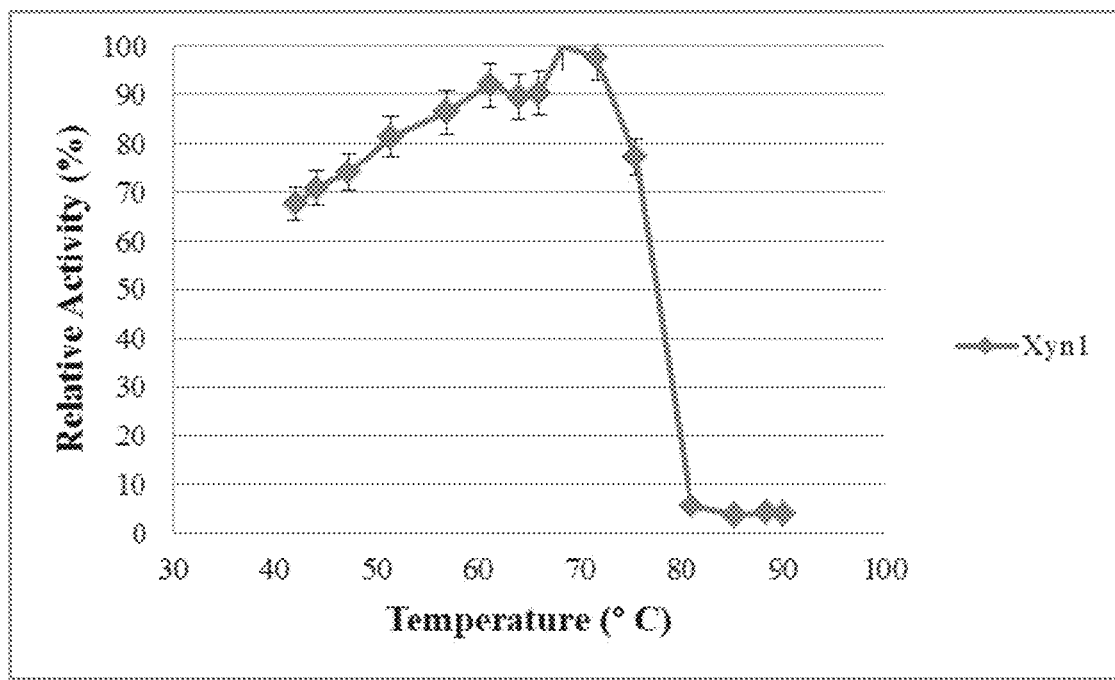
FIG. 7 illustrates temperature versus activity profiles of xyn1.

Temperature versus activity profiles were obtained according to the modified methods of Miller, et al. 1959. The profiles were obtained by carrying out the xylanase assay as described herein in triplicate at different temperatures for both the pure and crude enzyme. Temperatures in the range of 45-90° C. were used. The relative activity at the different temperature values was calculated as a percentage of activity at the optimum temperature. Temperature values versus percentage relative activities were plotted to yield the temperature profile for the crude and purified xylanase. The results were plotted as either percentage relative activity or specific activity verses temperature values (FIG. 7).

Example 4

Stability Profiles

Figure 8:
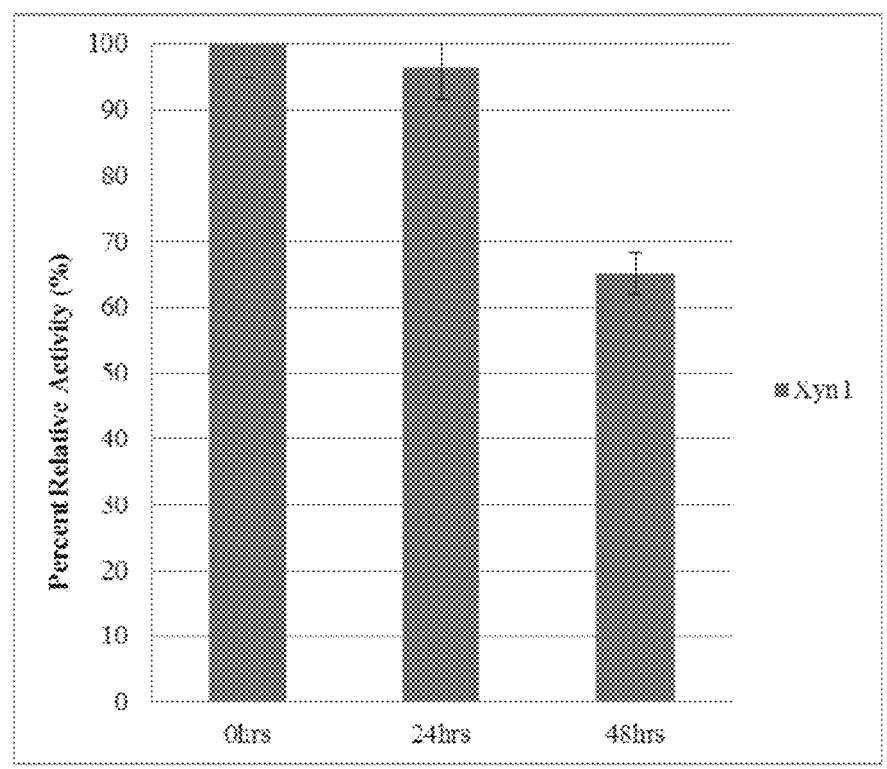
FIG. 8 illustrates the stability of xyn1 at 65° C. for prolonged incubations.

The stability profiles were obtained according to the modified methods of de Lemos Esteves et al., 2004; Georis et al., 2000; and Miller, 1959. A concentrated xylanase enzyme in 100 mM citrate buffer and 20% glycerol at the optimum pH and 65° C. of the respective xylanases for up to 48 h. Each extracted sample was assayed in triplicate for xylanase activity as described herein. The relative activity remaining was expressed as a percentage of the optimum activity observed. Incubation time versus percentage relative activity was plotted to yield the stability profile for the crude and purified xylanase (FIG. 8).

Example 5

Determination of Substrate Specificity

The substrate specificity of xyn1 was determined with respect to the substrates xylan from beechwood, xylan from beechwood, azo-wheatarabinoxylan, CM-cellulose, Avicel, p-nitrophenyl cellobioside, p-nitrophenyl xylopranoside. The first 5 substrates listed were tested as described herein by substituting 1% solutions of each substrate in place of xylan from beechwood. For the p-nitrophenyl-linked substrates, the assay systems contained either 500 µL or 100 µL 2.5 mM p-nitrophenyl-B-D-xylopyranoside/1 mM p-nitrophenyl cellobioside in 100/150 mM citrate buffer as substrates. The appropriate dilution of enzyme in dH2O was added to the appropriate substrate. The reaction was allowed to proceed for 15 min at the required temperature and was stopped by the addition of 1M sodium carbonate solution. Both substrate solution and enzyme were equilibrated to assay temperature prior to initiation of the reaction. An assay blank contained enzyme and substrate solution, which were incubated separately for the duration of the reaction period and mixed only after addition of stopping solution to the substrate. The assays and blanks were each carried out in quadruplicate. The absorbance of each sample was measured at 405 nm with a UV-visible spectrophotometer, blanked with dH2O.

Figure 9:
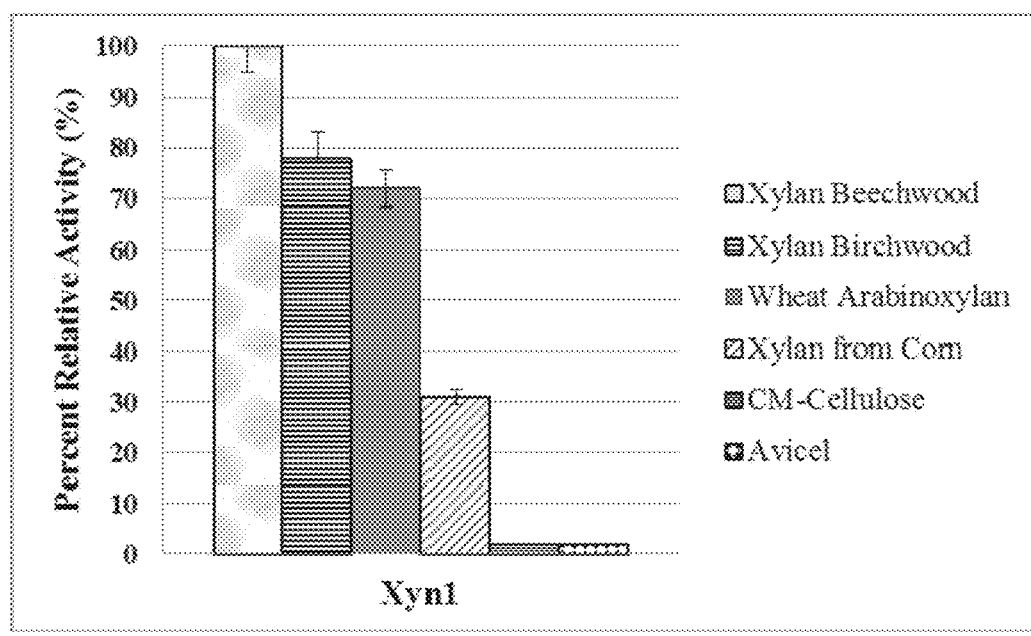
FIG. 9 illustrates substrate specificity of xyn1.

As the hydrolysis of p-nitrophenol-B-D-xylopyranoside and p-nitrophenyl cellobioside leads to the release of the p-nitrophenyl conjugate, a standard curve of p-nitrophenyl concentration verses absorbance at 405 nm was constructed to quantify the amount released during the assay. P-nitrophenyl standard solutions were prepared in quadruplicate by diluting a stock solution of p-nitrophenyl in 100 mM citrate buffer at the appropriate pH. Standard solutions ranged from 0-400 nmol/ml 4-nitrophenol. Construction of the standard curve was carried out by mixing the required amount of standard solutions with the required amount of stopping solution and subsequently determining absorbency values at 405 nm. From the standard curve, the amount of p-nitrophenyl released during the assay could be determined and this was used to calculate the activity the xylanases displayed towards xylopyranoside and cellobioside substrates (FIG. 9).

Example 6

Protein Engineering

The xyn1 nucleic acid sequence underwent protein engineering whereby a carbohydrate binding domain (CBM1) was fused to the C-terminal of the xyn1 nucleic acid sequence.

The nucleic acid sequence of CBM1 was:

```
AGCACCACCTACATCATCTCGCCGACGACGTCTGTCGGAACGGGCACGAC

GACCTCGAGCGGCGGAAGCGGCGGCACGACTGGCGTGGCCCAGCATTGGG

AGCAGTGCGGTGGACTGGGCTGGACTGGTCCGACGGTTTGCGCAAGTGGC

TACACTTGCACTGTCATCAATGAGTATTACTCGCAGTGTCTG
```

The nucleic acid sequence of the mature fused nucleic acid sequence:

```
TTGCTATTCAACTCGAACCTCACATCTCCTCCATGGCTCAATGATCTCGC

ACAGAGGCGTGGCAAGCTGTGGTTTGGCACGGCAGCTGACATCCCCGGTC

CAGAGCAGCAGGATACGAACTACATGACCATCCTGAATGATACGAAGATA

TTTGGGGAATTGACGCCTGCGAATTATATGAAGTTCGAATACACTGAACC

ATCGCCCAATGTCTTCAACTACTCTGGCGGCGACACCATCCTGGCCATCG

CCGAAAACCACGGCAAGCGCGTTCGCTGCCACAACCTCATCTGGGTCAGC

CAGCTGCCCGACTGGGTGGTGAACGGCAGCTGGACAGCGGCGAGCCTCAC

AGCGGTGATGAAGACGCACATCACGAACCTGATCACGCACTGGGGAGGGC

GGTGCTACTCGTGGGACGTGGTCAACGAGGCGCTGGCGGCGAACGGGTCG

TGGGCGTCCAGCATCTGGTACGACACCATCGGGCCCGAGTACTTCTTCCT

CGCGTACCGGTTTGCGCAGGAGGCGGTCGAAAAGACCGGCCAGGACATCA

AGCTGTACTACAATGACTACGGGATCGAGGCGCCCGGTCCCAAGACGACG

GCGGCGTACAACCTGGTCAAGGAGCTGCAGGCGCGAGGCATCCGGATCGA

TGGCGTGGGGTTGGAGTCGCATTTCGAAGTGGGCGCGACGCCATCCAAGG

ACGCGCAGGTTGAGGCCAAGCAGGGGTTTTTGGATCTGGGGGTCGATGTT

GTCGTCACGGAGCTGGATGTCAGATTCCCGGAGGGGCCGTTCTACACGGC

GGCGGGTGAGAAGCAGCAGGCGCAGGACTATTATGATACGGTGGCGAGCT

GCGTGGAGGTTGGTCCTCGGTGTGTGGGCATCACGGTGTGGGATTTTGAC

GATGCGTATTCGTGGGTGCCGTCATCGTTTCCTGGACAGGGAGCGGCTGA

TCTGTATAATGGGACGTTGCAGCGGAAGCCGGCGTACTATGCGGTGGCAG

AGGCATTGCAGGGGGTGAGTTGTAGTGTGTGCAGCACCACCTACATCATC

TCGCCGACGACGTCTGTCGGAACGGGCACGACGACCTCGAGCGGCGGAAG

CGGCGGCACGACTGGCGTGGCCCAGCATTGGGAGCAGTGCGGTGGACTGG

GCTGGACTGGTCCGACGGTTTGCGCAAGTGGCTACACTTGCACTGTCATC

AATGAGTATTACTCGCAGTGTCTG.
```

Figure 10:
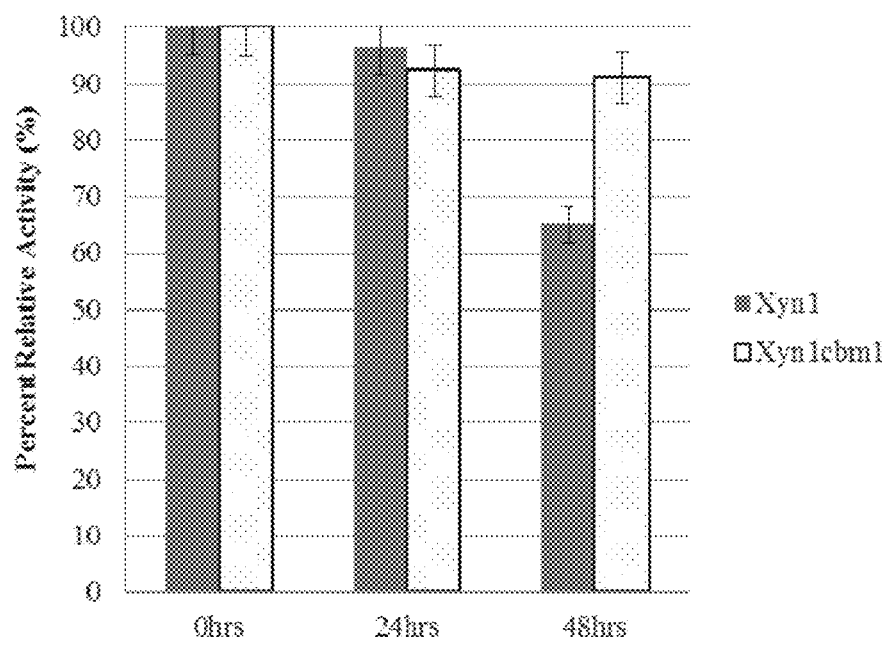
FIG. 10 illustrates thermos-stability of xyn1.

The addition of this CBM region increased the performance of the enzyme in the form that the thermo-stability of the xyn1 sequence where by over 90% relative activity remained for the engineered protein xyn1cbm1 after 48 hrs of incubation at 65° C. (FIG. 10).

Accordingly, the present invention provides isolated polynucleotides, isolated polypeptides encoded by the polynucleotides, any vector or plasmid holding or expressing the polynucleotides or polypeptides, any host cell holding or expressing the polynucleotides or polypeptides, the use of the polynucleotides or polypeptides for lignocellulose degradation, the use of the polynucleotides or polypeptides for xylan degradation, the use of the polynucleotides or polypeptides for polysaccharide degradation, the use of any part of the polynucleotides or polypeptides including signal peptides, catalytic domains, binding domains, and/or insertion domains for any industrial application including, but not limited to, the production of biofuels, in the paper and pulp industry, in clothing or leather softening, in the food industry such as baking, etc.

The invention thus provides isolated polypeptides that have been surprisingly found to have activity at an acid pH range, but also retained about 90% relative activity at such pH range (for example, at pH 3). The isolated polypeptides also have xylanase degradation activity against a number of xylan substrates, such that the isolated polypeptides can be considered to be "true" xylanases (that is, having xylanase degradation activity, specific xylanase degradation activity, for example xylanase degradation activity in respect of specific xylans, or solely xylanase degradation activity, for example not having activity on a substrate other than xylan). For example, the isolated polypeptides have xylanase degradation activity in respect of xylan from beech wood (about 100%), xylan from birchwood (about 78%) and wheat arabinoxylan (about 72%). Moreover, as an example, the isolated polypeptides have limited or no activity in respect of barley beta glucan, CM-Cellulose or xylo-glucan.

Although there are many xylanases isolated from *R. emersonii*, there is much evidence to suggest that the xylanolytic profile of this fungus differs greatly from strain to strain. For example other known xylanases have been isolated from *R. emersonii*, but are only isolatable from specific strains of *R. emersonii*, for example, *R. emersonii* IM1393751. The polypeptides of the present invention are polypeptides isolated or derived from *R. emersonii* strain IM116815. The polypeptides of the present invention have an apparent molecular weight of about 50.1-about 81.5 kDa (when glycosylated), and about 41.5 kDa when de-glycosylated, activity at an optimum temperature of about 70° C., pH optima of about pH 4, with high relative activity remaining at acidic pH values (for example, about 73% at about pH 2.5), with activity specifically displayed against xylan substrates.

The present invention therefore provides the advantages of enabling the utilization of excess lignocellulosic waste generated annually through various industries as a source of carbon, nitrogen, and various other value-added products; improving industrial applications including the cost and associated problems of carrying out industrial hydrolysis reactions at 50° C. or under.

The invention claimed is:

1. An isolated recombinant polypeptide having xylanase activity and comprising amino acid residues 19-362 of the amino acid sequence defined in SEQ ID NO: 1, and wherein the isolated recombinant polypeptide does not comprise amino acid residues 1-18 of the amino acid sequence defined in SEQ ID NO: 1, or an analogue thereof having at least 95% sequence identity to the amino acid sequence defined in SEQ ID NO: 1, wherein the analogue has xylanase activity, and wherein the analogue does not comprise amino acid residues 1-18 of the amino acid sequence defined in SEQ ID NO: 1.

2. An isolated recombinant polypeptide according to claim 1, wherein the isolated polypeptide has a molecular weight of at least 47.5 kDa.

3. An isolated recombinant polypeptide according to claim 1, wherein the isolated polypeptide or analogue thereof has an enzymatic activity capable of degrading at least one of the following substrates:
   xylan from beechwood,
   azo-wheatarabinoxylan,
   wheatarabinoxylan,
   xylopranoside; and/or
   p-nitrophenyl xylopranoside.

4. An isolated recombinant polypeptide according to claim 1, wherein the isolated polypeptide analogue has at least 99% sequence identity to the amino acid sequence defined in SEQ ID NO: 1.

5. An isolated recombinant polynucleotide comprising the nucleic acid sequence defined in SEQ ID NO:2, or a variant thereof having at least 85% sequence identity to the nucleic acid sequence defined in SEQ ID NO: 2, wherein the isolated recombinant polynucleotide encodes the isolated recombinant polypeptide of claim 1.

6. A vector comprising the isolated polynucleotide according to claim 5.

7. A recombinant host cell comprising the vector according to claim 6.

8. A method of preparing a recombinant host cell, the method comprising the steps of:
   (a) providing a host cell; and
   (b) introducing into the host cell the vector according to claim 6.

9. A method of preparing an isolated recombinant polypeptide having xylanase activity; the method comprising the steps of:
   (a) providing a host cell;
   (b) introducing into the host cell the vector according to claim 6;

(c) transcribing the vector to obtain a ribonucleic acid; and (d) translating the ribonucleic acid to obtain the isolated polypeptide.

10. A method of degrading lignocellulose biomass, the method comprising the steps of:

(a) providing a lignocellulose biomass; and (b) contacting the lignocellulose biomass with the isolated recombinant polypeptide according to claim 1.

11. A method of degrading lignocellulose biomass, the method comprising the steps of:

(a) providing a lignocellulose biomass; and (b) contacting the lignocellulose biomass with the recombinant host cell according to claim 7.

12. A method according to claim 10, wherein the contacting step (b) of the method of degrading lignocellulose biomass is conducted at a pH of 3.0-6.0.

13. A method according to claim 10, wherein the contacting step (b) of the method of degrading lignocellulose biomass is conducted at a temperature of 45-90° C.

14. The isolated recombinant polypeptide of claim 1, wherein the isolated recombinant polypeptide further comprises a carbohydrate binding domain (CBM1) fused to a C-terminus, wherein the CBM1 is defined in SEQ ID NO: 5 and is fused to the C-terminus of the peptide defined in SEQ ID NO: 1.

15. The isolated recombinant polypeptide of claim 1, wherein the isolated recombinant polypeptide further comprises a purification tag.

16. The isolated recombinant polypeptide of claim 15, wherein the purification tag is a polyhistidine tag.

17. An isolated polypeptide according to claim 1, wherein the isolated polypeptide or analogue thereof has greater xylan from beechwood degradation activity than any one of azo-wheatarabinoxylan degradation activity, wheatarabinoxylan degradation activity, xylopranoside degradation activity and p-nitrophenyl xylopranoside degradation activity.

18. An isolated polypeptide according to claim 1 wherein the isolated polypeptide or analogue thereof has greater xylan from beechwood degradation activity than wheatarabinoxylan degradation activity.

19. An isolated polypeptide according to claim 1, wherein the isolated polypeptide or analogue thereof has activity at an acid pH range, including about 90% relative activity at pH 3.

20. A vector according to claim 6 comprising a promoter operatively linked to the polynucleotide, and wherein the promoter comprises the nucleotide sequence defined in SEQ ID No. 4.

21. The isolated recombinant polypeptide of claim 1, wherein the isolated recombinant polypeptide or the analogue thereof has no cellulase activity.

* * * * *